(12) United States Patent
Yarnall et al.

(10) Patent No.: US 6,331,703 B1
(45) Date of Patent: Dec. 18, 2001

(54) GUIDANCE METHOD FOR RADIATION DETECTION

(75) Inventors: Stephen T. Yarnall, Poway, CA (US); Mark W. DiFrancesco, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/266,961

(22) Filed: Mar. 12, 1999

(51) Int. Cl.[7] ...................................................... A61B 5/02
(52) U.S. Cl. .......................................................... 250/336.1
(58) Field of Search ........................................... 250/336.1

(56) References Cited

U.S. PATENT DOCUMENTS

| | | | |
|---|---|---|---|
| 4,665,486 | 5/1987 | Schultz | 364/422 |
| 4,782,850 | 11/1988 | Martin, Jr. et al. . | |
| 4,801,803 | 1/1989 | Denen et al. . | |
| 4,889,991 | 12/1989 | Ramsey et al. | 250/336.1 |
| 4,893,013 | 1/1990 | Denen et al. | 250/336.1 |
| 5,008,546 | 4/1991 | Mazziotta et al. | 250/366 |
| 5,070,878 | 12/1991 | Denen | 128/659 |
| 5,151,598 | 9/1992 | Denen | 250/336.1 |
| 5,246,005 | 9/1993 | Carroll et al. . | |
| 5,383,456 | 1/1995 | Arnold et al. . | |
| 5,428,223 | 6/1995 | Jatteau et al. | 250/363.06 |
| 5,441,050 | 8/1995 | Thurston et al. | 128/659 |
| 5,732,704 | 3/1998 | Thurston et al. | 128/659 |
| 5,744,805 | 4/1998 | Raylman et al. | 250/370.01 |
| 5,853,364 | * 12/1998 | Baker, Jr. et al. | 600/300 |
| 5,857,463 | 1/1999 | Thurston et al. | 128/659 |

FOREIGN PATENT DOCUMENTS

| | | |
|---|---|---|
| 284542 B2 | 4/1992 | (EP) . |
| 369927 B1 | 7/1993 | (EP) . |
| 603111 A2 | 6/1994 | (EP) . |
| 371903 B1 | 4/1996 | (EP) . |
| 535160 B1 | 7/1999 | (EP) . |
| 88/07209 A1 | 9/1988 | (WO) . |
| 93/18797 A1 | 9/1993 | (WO) . |
| 97/42524 A1 | 11/1997 | (WO) . |

OTHER PUBLICATIONS

"Intraoperative Probe–Directed Immunodetection Using a Monoclonal Antibody" Patrick J. O'Dwyer, M.D. et al., Monoclonal Antibody Immunodetection—O'Dwyer et al, Arch Surg—vol. 121, Dec. 1986.

"Radioimmunoguided Surgery: Introperative Use of Monoclonal Antibody 17–1A in Colorectal Cancer" E.W. Martin, Jr. et al., Hybridoma, vol. 5, Suppl. 1, 1986, Mary Ann Liebert, Inc. Publishers.

(List continued on next page.)

*Primary Examiner*—Constantine Hannaher
*Assistant Examiner*—Otilia Gabor
(74) *Attorney, Agent, or Firm*—Bernard Shay

(57) ABSTRACT

A non-linear guidance method for radiation detection is described herein wherein a heuristic non-linear radiation detection method is utilized is for the location of sentinel nodes for staging cancer. The method of radiation detection described herein includes the steps of: Generating radiation decay rate counts wherein the counts are a sum of detected radiation decay events over a time interval; loading the counts into an array; summing selected elements of the array to generate a total count and a plurality of candidate counts; comparing the total count to one of the candidate counts to determine whether the one of the candidate counts is statistically different from the total count; using the statistically different one of the candidate counts as an output count rate; and generating an output signal using the output count rate to determine the characteristics of the output signal.

11 Claims, 12 Drawing Sheets

OTHER PUBLICATIONS

Portable Gamma Probe for Radioimmune Localization of Experimental Colon Tumor Xenografts[1], Delmar R. Aitken, M.D. et al., Journal of Surgical Research 36, 480–489 (1984).

"CEA–Directed Second–look Surgery in the Asymptomatic Patient after Primary Reaction of Colorectal Carcinoma" Edward W. Martin, Jr. et al., Ann. Surg., 1985, vol. 202, No. 3, 310–317.

"Intraoperative Radioimmunodetection of Colorectal Tumor With a Hand–Held Radiation Detector", Edward T. Martin, M.D. et al., The American Journal of Surgery, vol. 150, Dec. 1985, 672–675.

"Lymphatic Mapping and Sentinel Lymphadenectomy for Breast Cancer" Armando E. Guilano, M.D. et al., Annals of Surgery, vol. 220, No. 3, 391–401, ©1994 J.B. Lippincott Company.

"Cancer Principles & Practice of Oncology", Fourth Edition, Jay R. Harris et al., J.B. Lippincott Company, Philadelphia ©1993, vol. 1, Chapter 40, pp. 1264–1332.

"Lymphatic Mapping and Sentinel", (Armando E. Giuliano et al., Annuals of Surgery (1994) vol. 220 No. 3. 391–401.

"Cancer of the Breast", (Jay R. Harris et al., Cancer: Principles & Practice of Oncology, Fourth edition (1993) Chapter 40.

* cited by examiner

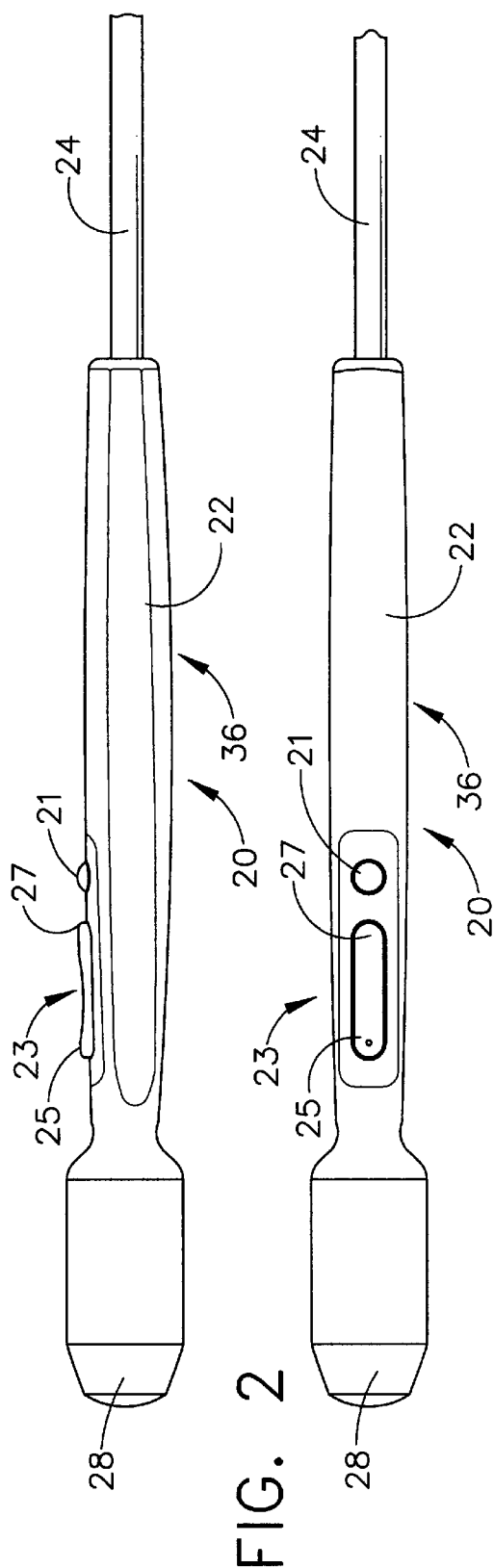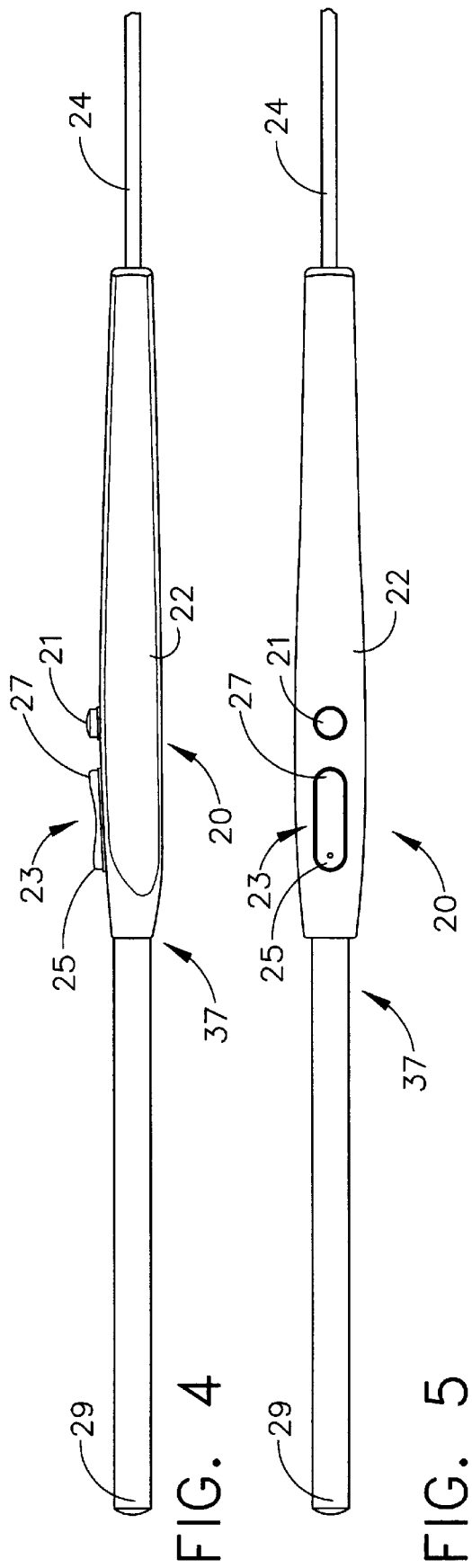
FIG. 2  FIG. 3  FIG. 4  FIG. 5

GUIDANCE METHOD FOR RADIATION DETECTION

FIELD OF THE INVENTION

The present invention relates, in general, to non-linear guidance methods for radiation detection and, more particularly, to heuristic non-linear radiation detection methods utilized for the location of sentinel nodes for staging cancer.

BACKGROUND OF THE INVENTION

An evaluation of the presence or absence of tumor metastasis or invasion has been a significant issue for achieving an effective treatment for cancer patients. The involvement of the lymph system in tumor metastasis is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis occurring in consequence of lymph drainage will result in an initial location or positioning of neoplastic cells at certain lymph nodes typically deemed "regional nodes" within a pertinent lymph drainage basin. Some cancers, such as those encountered in the breast, will evidence somewhat predictable nodal involvement.

In designing forms of cancer disease management, efforts are directed to the identification of affected lymph nodes. For cancers such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer, See generally, "Cancer, Principles and Practice of Oncology", vol. 1, 4th ed. DeVita, Jr., et al., chapter 40, Harris, et al., J. P. Lippincott Co., Philadelphia, Pa. 1993.

The axilla is a triangular region bounded by the axillary vein superiorly, the latissimus dorsi laterally, and the serratus anterior medially, With some diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment of fatty tissue and visualization of them necessarily is limited. Such dissection will pose risks of cutting the long thoracic nerve, the thoracic-dorsal nerve, the nerve to the pectoralis major, or the axillary vein. Morbidity may occur in some cases due to regional node removal and patients are known to frequently discuss a numbing of the arm region following the procedure.

While this form of axillary lymph node dissection has been the conventional approach to determining nodal metastatic involvement, more recent data suggest that less radical axillary node evaluation procedures may generate equivalent information for staging and patient management, but with far more limited dissection and resultant trauma, as discussed below. A procedure to moderate the otherwise somewhat radical axillary lymph node dissection common in staging breast cancer has been described generally in "Lymphatic Mapping and Sentinel Lymphadenectomy for Breast Cancer" by Guiliano, A. E.; Kirgan, B. M.; Guenther, J. M.; and Morton, D. L., *Annals of Surgery*, vol 220, no. 3: 391–401, 1994. With the procedure, in general, a vital blue dye is injected into the breast mass and surrounding breast parenchyma. Following a relatively short interval, a transverse incision is made just below the hair-bearing region of the axilla. Blunt dissection is performed until a lymphatic tract or duct leading to a blue stained node is identified. The lymph duct, having a blue color, provides a guide path leading to the location of the most proximal lymph node, also called the sentinel node. This sentinel node is excised and evaluated. Blunt dissection using vital dyes for guidance requires considerable surgical experience and talent associated with the delicate task of following the blue duct (a ruptured dye-carrying duct can be problematic). The ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes.

Lymph node involvement in metastasis also has been the subject of investigation in other quite different forms of cancer such as colon cancer. This has been through the utilization of a hand-held radiation responsive probe. The U.S. Pat. No. 4,782,840 by Martin et al. entitled "Method for Locating, Differentiating, and Removing Neoplasms", issued Nov. 8, 1988, reviews the approaches of nuclear medicine for locating colon tumors. The patent discloses a method for locating, differentiating, and removing neoplasms by using a radio-labeled antibody in conjunction with the radiation detection probe, which the surgeon may use intraoperatively in order to detect the sites of radioactivity. Because of the proximity of the detection probe to the labeled antibody, the faint radiation emanating from occult sites becomes detectable because, in part, of the inherent application of the approximate inverse square law of radiation propagation. This evaluation also may be employed with certain more minimally invasive procedures as described by M. W. Arnold, and M. O. Thurston, in U.S. Pat. No. 5,383,456, entitled "Radiation-Based Laparoscopic Method for Determining Treatment Modality" issued Jan. 24, 1995.

Thurston et al. discloses a radiation based method for locating and differentiating sentinel nodes in U.S. Pat. No. 5,732,704. The method identifies a sentinel lymph node located within a grouping of regional nodes at a lymph drainage basin associated with neoplastic tissue. A radiopharmaceutical is injected at the situs of the neoplastic tissue. The radiopharmaceutical migrates along a lymph duct toward the drainage basin containing the sentinel node. A hand-held probe with a forwardly disposed radiation detector crystal is maneuvered along the duct while the clinician observes a graphical readout of count rate amplitudes to determine when the probe is aligned with the duct. The region containing the sentinel node is identified when the count rate at the probe substantially increases. Following incision, the probe is maneuvered utilizing a sound output in connection with actuation of the probe to establish increasing count rate thresholds, followed by incremental movements, until the threshold is not reached and no sound cue is given the surgeon. At this point of the maneuvering of the probe, its detector will be adjacent to the sentinel node, which then may be removed. Although this procedure is currently possible, the random nature of decay of the radiopharmaceutical, and the low doses desired to minimize patient and clinician exposure, provide less than optimal guidance of current devices such as those described in U.S. Pat. No. 5,732,704.

An attempt to compensate for the difficulty in determining count rates has been described in U.S. Pat. No. 4,889,991. An enhanced signal treatment algorithm was developed utilizing weighted averaging and slew rate limiting to provide enhanced audio output for cueing an operator about a radiation detector probe's position relative to a radiolabeled sentinel node. It describes the use of a squelch determined by establishing a base count rate for background radiation. Where a statistically significant count rate is encountered, and depending upon the system's operational mode, the presence of a tumor will be defined as, for example, a count rate of three standard deviations above the base count rate. However systems utilizing signal processing algorithms such as those described in U.S. Pat. No. 4,889,991 lose some precision and response time due to the squelching and averaging of count rate information. Count rate averaging and weighted averaging can be characterized as linear filters, and specifically as low-pass filters. Low pass filters tend to slow system response time and reduce the strength of the response of the system.

Therefore, it would be advantageous to provide a radiation detection and guidance method that has an improved response rate to precisely locate sentinel nodes. It would be advantageous to provide a count rate determination method that is less hindered by the tradeoff between system stability and system response time inherent in current linear algorithms. It would also be advantageous to provide a radiation detection and guidance method that provides conditioned output count rate information to reduce erroneous or spurious changes in feedback to the operator. It would further be advantageous to provide improved count rate information to actual changes of count rates while removing rate change artifacts due to the random nature of radiation decay.

SUMMARY OF THE INVENTION

Described is a non-linear guidance method for radiation detection and, more particularly, a heuristic non-linear radiation detection method utilized for the location of sentinel nodes for staging cancer. The method of radiation detection includes the steps of generating radiation decay count rates wherein the count rates comprise a sum of detected radiation decay events over a time interval, loading the count rates into an array, summing selected elements of the array to generate a total count and a plurality of candidate counts, comparing the total count to one of the candidate counts to determine whether the one of the candidate counts is statistically different from the total count, using the statistically different one of the candidate counts as an output count rate, and generating an output signal using the output count rate to determine the characteristics of the output signal.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is a side elevational view of the scanning probe of FIG. 1;

FIG. 3 is a plan view of the scanning probe;

FIG. 4 is a side elevational view of the targeting probe of FIG. 1;

FIG. 5 is a plan view of the targeting probe;

DETAILED DESCRIPTION OF THE INVENTION

Figure 1:
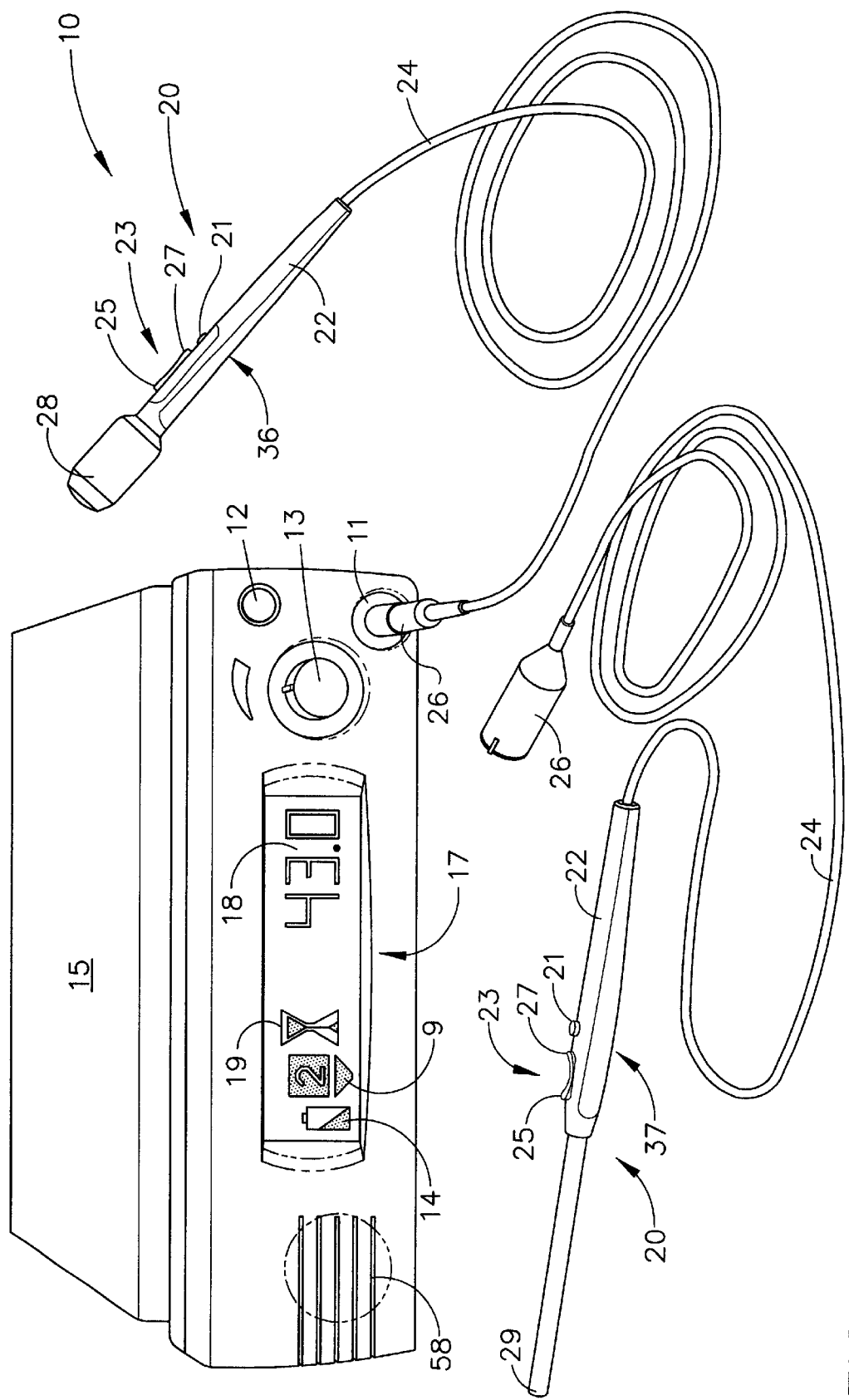
FIG. 1 is a perspective view of an audible guidance system in accordance with the present invention, including a control unit, a scanning probe and a targeting probe.

FIG. 1 is a perspective view of an audible guidance system 10 in accordance with the present invention. Audible guidance system 10 includes a control unit 15, a scanning probe 36 and a targeting probe 37. Control unit 15 of audible guidance system 10 may be used with either scanning probe 36, targeting probe 37, or other suitable radiation detection devices. For convenience, probes 36 and 37 may referred to generically as gamma probe 20. In FIG. 1, control unit 15 includes a volume set button 12, a volume knob 13, a cable input 11, a display 17 and an audio speaker 58. Display 17 includes a visual count rate indicator 18, a wait indicator 19, a range indicator 9, and a battery indicator 14.

Gamma probes 36 and 37 both include a probe housing 22, a cable 24, a connector 26, audio range switch 23 and mode button 21. Scanning probe 36 and targeting probe 37 include gamma detector assemblies 28 and 29 respectively.

Scanning probe 36 is particularly adapted for gross location of radio-active hot spots while gamma detector assembly 29 is particularly adapted for fine location of radio-active hot spots. As will be appreciated by those skilled in the art, detector assemblies 28 and 29 vary in size and sensitivity according to the function they are designed to perform. A gamma probe 20 which includes a scanning detector assembly 28 is called a scanning probe 36. A gamma probe 20 which includes a targeting detector assembly 29 is called a targeting probe 37. Audio range switch 23 includes a shift up button 25 and a shift down button 27.

FIGS. 2–5 provide side and plan views of scanning detector 36 and targeting detector 37. FIG. 2 is a side elevational view of scanning probe 36. FIG. 2 illustrates the relative locations of scanning detector assembly 28, housing 22, audio range switch 23, cable 24 and mode button 21 in scanning probe 36. FIG. 3 is a plan view of scanning probe 36. FIG. 4 is a side elevational view of targeting probe 37. FIG. 4 illustrates the relative locations of targeting detector assembly 29, housing 22, audio range switch 23, cable 24 and mode button 21 in scanning probe 37. FIG. 5 is a plan view of targeting probe 37.

Figure 6:
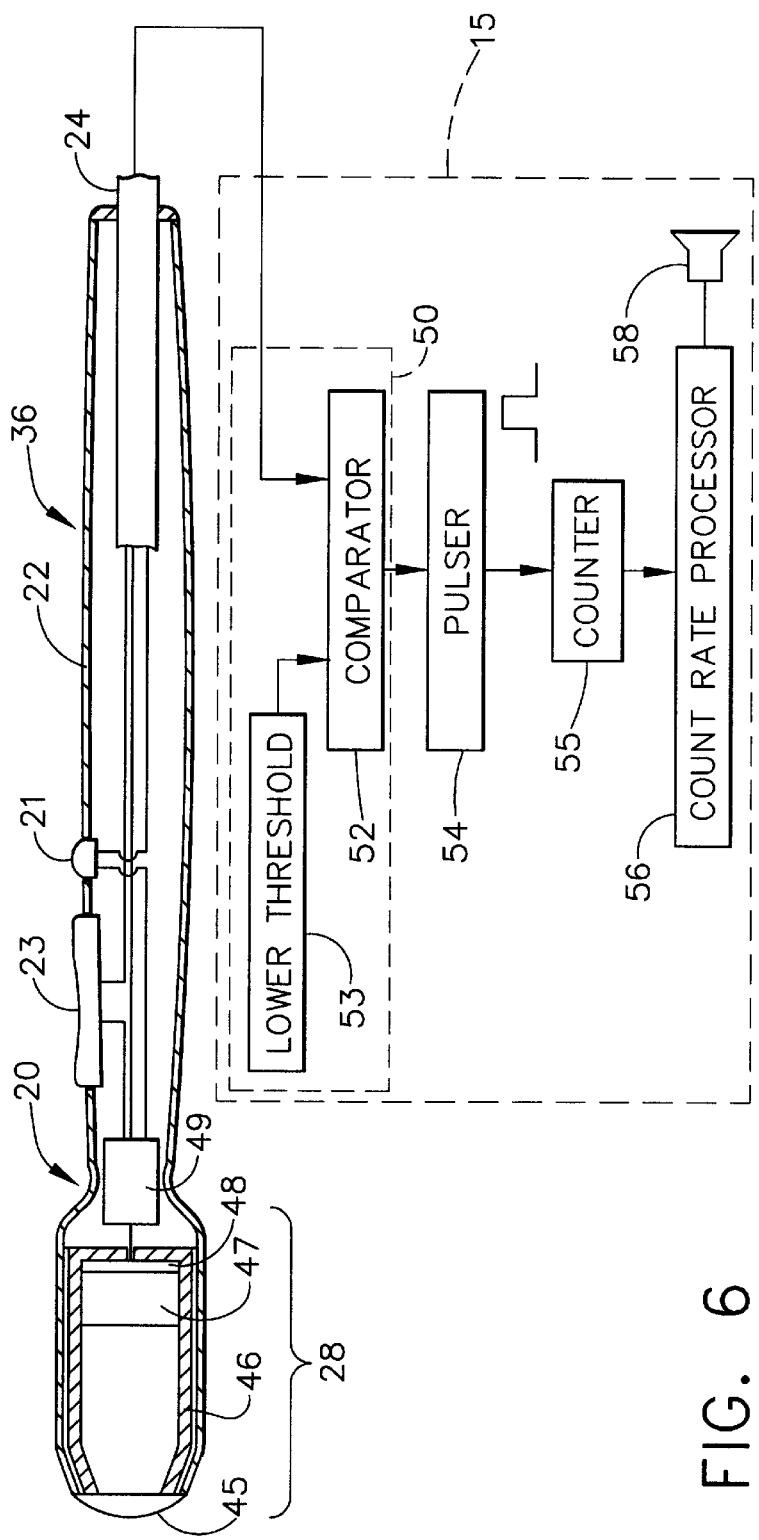
FIG. 6 is a view in upright section of the scanning probe illustrating internal components in schematic form in cooperative relationship with other system components also in schematic form.

FIG. 6 is a schematic view in upright section illustrating the internal components of scanning probe 36 and their interconnection with control unit 15. Scanning probe 36 includes, within housing 22, a radiation transparent window 45, a collimator 46, a scintillator 47, a light detector 48, and, in the embodiment illustrated, a pre-amplifier 49 in proximity to light detector 48. Scanning probe 36 also includes, within housing 22, a cable 24 connectable to control unit 15 via connector 26 and cable input 11, as shown in FIG. 1. Scanning probe 36 is environmentally sealed to prevent body fluids from contacting the components inside probe housing 22. Scanning probe 36 may be a multi-patient use resterilizable instrument, or a single patient use disposable instrument.

Referring to FIG. 6 control unit 15 includes count rate processor 56 which utilizes a rate determination algorithm according to the present invention to calculate an output count rate which is used to select an output audio signal at speaker 58. Count rate processor 56 incorporates a rate determination algorithm, one embodiment of which in accordance with the present invention calculates, in a statistically valid way, a number indicative of a best current count rate. The best current count rate is a number which is used to decide whether to change the current audio feedback signal. Changes in the audio feedback signal are used to audibly indicate the relative position of the probe and the target. In particular, for clarity, the most recently calculated count rate is referred to as the "current count rate," the actual rate of decay of the radio-active isotope is referred to as the "actual count rate," and the count rate being used to select the appropriate output tone is referred to as the "prevailing count rate."

As illustrated in FIG. 6, control unit 15 includes a discriminator 50, a pulser 54, a counter 55, a count rate processor 56, and an audio speaker 58. In one embodiment of the present invention, the pulser 54 may be eliminated and the output of discriminator 50 may be fed to the counter 55. In the present embodiment, the input to discriminator 50 is a series of electrical signals which have an amplitude that is proportional to the energy content of the gamma rays which enter window 45 and strike scintillator 47. Discriminator 50 is a circuit adapted to filter out inputs resulting from stray gamma signals such as those which are generated outside the field of window 45 but enter window 45 as a result of Compton scattering in the field of window 45. Discriminator 50 includes a comparator 52. Using comparator 52, discriminator 50 filters out all signals generated by inputs to window 45 which are not above a predetermined lower threshold level 53 (e.g. approximately 110 keV). It will be understood that discriminator 50 may be further modified by, for example, adding a second comparator circuit, to filter signals generated by inputs which are within a predetermined energy range (e.g. approximately 140 keV+/−35 keV). The output of comparator 52 is processed by pulser 54.

Pulser 54 is an electronic circuit adapted to output an electronic pulse whenever the output of comparator 52 changes state. Thus, comparator 52 compares the lower threshold level 53 with the conditioned electrical signal, and triggers an output pulse from pulser 54 for every conditioned electrical signal form gamma probe 20 where the conditioned electrical signal is above the lower threshold. The output of pulser 54 is processed by counter 55 which is electrically connected to the pulser 54. Counter 55 counts the number of pulses generated by pulser 54 over a predetermined time interval (e.g. 64 milliseconds).

The output of counter 55 is a count rate which is processed by count rate processor 56. Count rate processor 56 is a computer processor which utilizes the algorithm set forth herein to convert the count rate output from counter 55 into an output signal which contains information useful in locating a sentinel node. The output signal from count rate processor 56 is an electronic output signal which may be heard through speaker 58.

Figure 7:
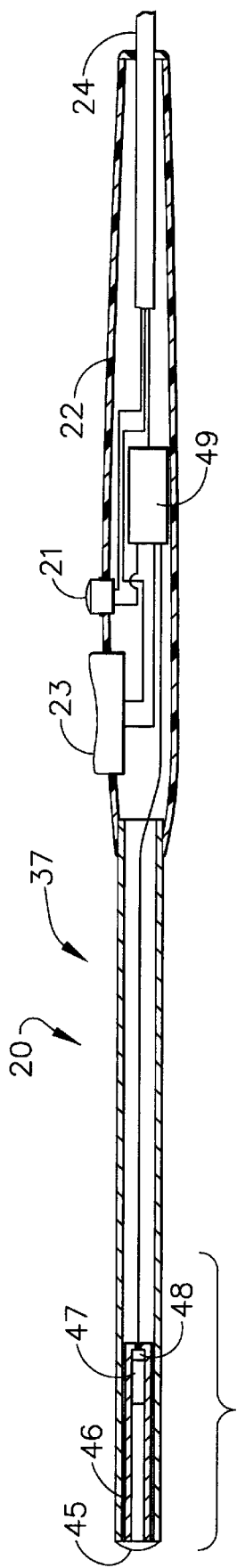
FIG. 7 is a view in upright section of the targeting probe illustrating internal components in schematic form.

FIG. 7 is a schematic view in upright section illustrating the internal components of targeting probe 37. Targeting probe 37 includes, within housing 22, a radiation transparent window 45, a collimator 46, a scintillator 47, a light detector 48, and, in the embodiment illustrated, a pre-amplifier 49 in proximity to light detector 48. It will be apparent to those of skill in the art that because window 45 and scintillator 47 are smaller in targeting detector assembly 29 than they are in scanning detector assembly 28, the sensitivity of scanning probe 36 will be higher than the sensitivity of targeting probe 37. Thus, scanning probe 36 is particularly adapted to identifying the general location of a sentinel node, by, for example, passing it over the skin of a patient. Targeting probe 37 is particularly adapted to locating the exact position of a sentinel node by, for example, passing it through the breast tissue of a patient. Targeting probe 37 also includes, within housing 22, a cable 24 connectable to control unit 15 via connector 26 and cable input 11, as shown in FIG. 1. Targeting probe 37 is environmentally sealed to prevent body fluids from contacting the components inside probe housing 22. Targeting probe 37 may be multi-patient use resterilizable instrument, or a single patient use disposable instrument.

Figure 8:
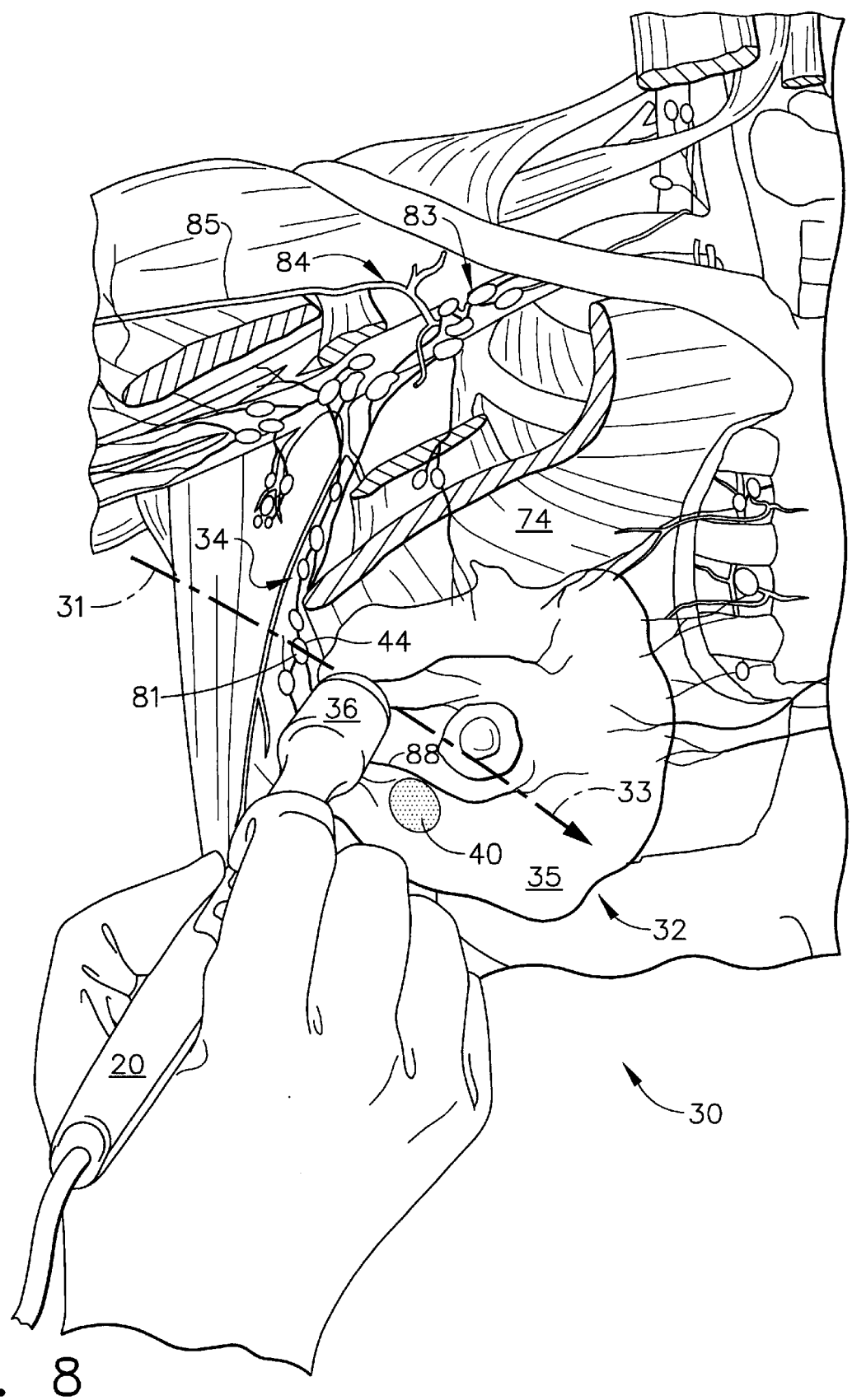
FIG. 8 is a right side anterior view of a patient illustrating a tumor site and lymph system exposed by successive cutaways of overlaying tissue.

The following is a brief description of a procedure utilizing a probe 20 to identify a sentinel node in accordance with the present invention. Prior to initiating a scan, a radio-active material, such as technetium 99 m sulfur colloid, is injected into the region of the cancerous tissue and allowed to drain into the surrounding lymph nodes. The lymph nodes that drain the tumor site will collect the radio-active material with those most directly connected to the tumor site, the sentinel nodes, collecting the most radio-active material. FIG. 8 is a right side anterior view of a portion of a human torso 30. In FIG. 8, human breast 35 includes a tumor 40, and lymph system 34, lymph duct 88, sentinel node 81, infraclavicular nodes 83 and axillary vein 85. In FIG. 8, the structures in torso 30 are exposed by successive cutaways of overlaying tissue. Gamma probe 20 is illustrated moving through scan region 32 from an initial posterior position 31, to anterior position 33. In FIG. 8, a sentinel node 81 is located along the scan path between initial posterior position 31 and anterior position 33. Referring to FIGS. 6 and 8, gamma probe 20 is adapted to detect radiation emanating from a source 44. Source 44 may be, for example, a radio-active isotope in sentinel node 81 that, upon a decay event, produces gamma radiation. Window 45 of gamma probe 20 allows radiation from source 44 to enter collimator 46. Collimator 46 generally stops the passage of radiation outside an angular viewing area. Radiation traveling along a path within the viewing area is allowed to impact scintillator 47. Scintillator 47 converts the radiation to light, which is converted to an electrical signal by light detector 48. A pre-amplifier 49 may be used to condition the electrical signal, which is then input to discriminator 50 of control unit 15.

Figure 9:
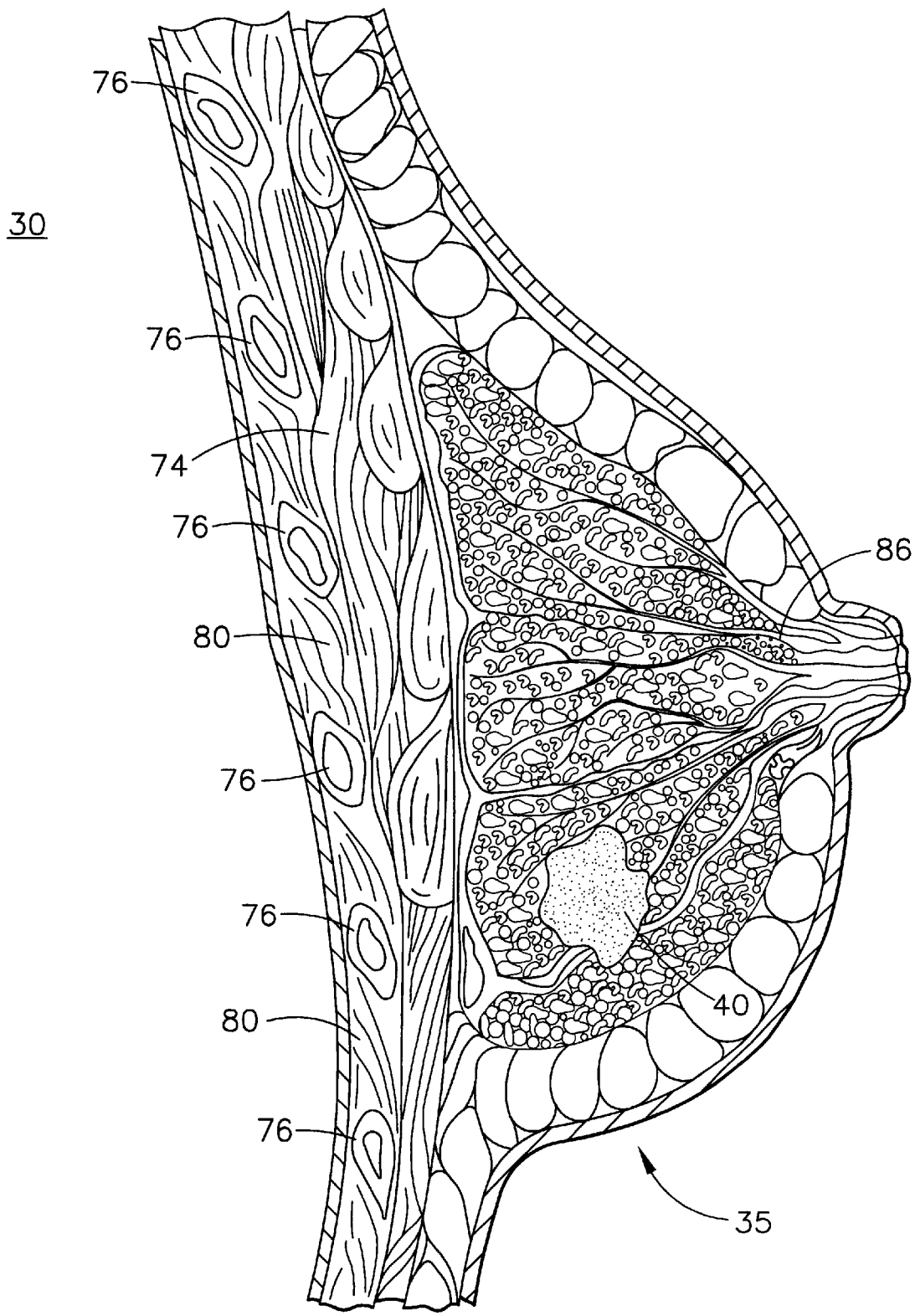
FIG. 9 is a sagittal section view of the patient in FIG. 8.

FIG. 9 is a sagittal section view of breast 35 further illustrating the relative location of tumor 40. As illustrated in FIG. 9, breast 35 includes tumor 40, lactiferous ductal system 86, ribs 76, pectoralis muscle 74, and intercostal muscle 80.

FIGS. 10–13 illustrate one embodiment of a count rate determination algorithm according to the present invention. In general, in a count rate determination algorithm according to the present invention, a long-term average count rate is calculated over a predetermined number of input periods and compared against a series of measured and calculated count rates. If any of the measured or calculated count rates represent a statistically significant change over the long-term average count rate, it is used to select the appropriate audio output tone. The measured or calculated count rate which differs in a statistically significant manner from the long-term average count rate and which provides the fastest system response is selected as the best estimate of the actual count rate. For example, using a measured count rate, such as, for example, the count rate in the first element of an array 60 (illustrated in decision block 101 of FIG. 10), if the measured count rate differs, in a statistically significant manner, from a long-term average count rate (e.g. the average of all the count rates in array 60), a count rate determination algorithm according to the present invention will respond immediately, using the measured count rate as the current count rate, without using count rate information from other positions within array 60. Alternatively, if the measured count rate does not differ from the long-term average count rate in a statistically significant way, then one or more calculated count rates, such as, for example, one or more short term average count rates, may be compared to the long-term average count rate to see whether any of the calculated count rates differ in a statistically significant way from the long-term average count rate. The first of the calculated count rates in this descending system time response order which differs from the long-term average count rate in a statistically significant way may then be used as the current count rate. Finally, if neither the measured count rate nor any of the calculated count rates differ from the long-term average count rate in a statistically significant manner, the long-term average count rate is used as the current count rate. A count rate determination algorithm according to the present invention is adapted to provide a faster response rate than a stable linear count rate determination algorithm, yet maintain desired operational stability. A count rate determination algorithm in accordance with the present invention will be described in more detail while referring to FIGS. 10–13.

The flow chart in FIGS. 10–13 is broken into sections, each section illustrating a portion of a count rate determination algorithm according to the present invention. In order to more clearly understand the steps of a count rate determination algorithm according to the present invention, the function of array 60 and its interaction with counter 55 will be more fully described. As described previously, counter 55 counts the number of pulses generated by pulser 54 over a predetermined time interval (e.g. 64 milliseconds). In one embodiment of the present invention, after every 64-millisecond interval the number of counts in the counter 55 is input to the first element of array 60, while the previous counts are shifted one element to the left. In an alternative embodiment of the present invention, the input to the first element array 60 may be squelched or limited by, for example, counting up to a predetermined limit and, if the number of counts within the 64-milisecond window exceeds the predetermined limit, the predetermined limit is used as the input to the first element of array 60. Array 60 may comprise, for example, sixteen elements numbered one through sixteen. Element one will contain the most recent count, element two will contain the count from the previous 64 millisecond's accumulation, element three will contain the count from the 64 millisecond accumulation that ended 128 milliseconds ago, etc. Every 64 milliseconds the counts contained in the sixteen elements of array 60 are shifted to the next higher element in array 60. The count in element 16 of array 60 is discarded and element 1 is loaded with the count contained in counter 55. In this embodiment of the present invention, the counts in the array 60 are evaluated at every 64 millisecond interval by a count rate determination algorithm according to the present invention to obtain the best estimate of the actual count rate, and determine if the prevailing count rate should be changed.

One embodiment of a count rate determination algorithm according to the present invention is illustrated in FIGS. 10–13. In calculation block 101 of FIG. 10 SUM1 represents the count rate in element 1 of array 60 which is, according to this embodiment of the present invention, the most recent count rate measured by counter 55. SUM2 represents the sum of the count rates from the first and second elements of array 60. SUM4 represents the sum of the count rates from the first four elements of array 60. SUM8 represents the sum of the count rates from the first eight elements of array 60. SUM16 represents the sum of the count rates from all sixteen elements of the array 60. Thus, in this embodiment of the present invention: SUM1 is the measured count rate; SUM2, SUM4 and SUM8 are the calculated count rates; and SUM16 is the long-term average count rate. It will be appreciated that, for comparison purposes the measured count rate and the calculated count rates are normalized with respect to the long-term average count rate.

Figure 10:
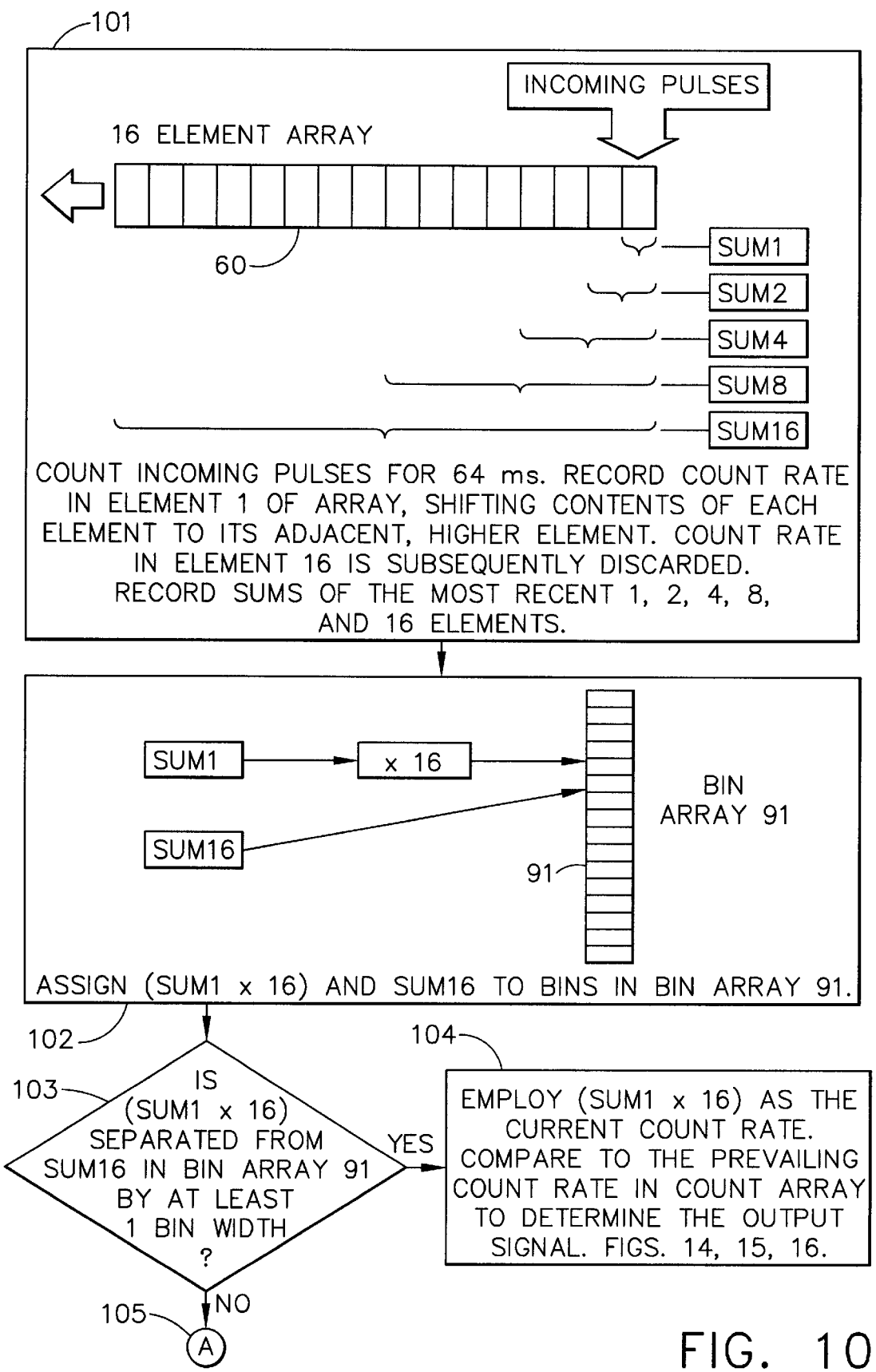
FIG. 10 is the portion of a flowchart illustrating a method of data analysis in accordance with the present invention relating to SUM1.

In FIG. 10, calculation block 102 illustrates a method of normalizing SUM1 and comparing SUM1 to SUM16 in accordance with the present invention. FIG. 10 illustrates calculation block 101, calculation block 102, decision 103, decision yes result 104, and point A 105. The step of the count rate determination algorithm illustrated in calculation block 102 determines if a normalized SUM1 is statistically distinct from SUM16. One method of accomplishing this is by developing a bin array 91 which includes a series of bins, each bin containing a range of normalized count rates, wherein the normalized count rates in each bin are selected to be statistically different from the normalized count rates in bins one bin away from the selected bin. Normalized count rate values for each bin in bin array 91 are predetermined and, in the present embodiment may be calculated using statistical t-tests and empirically adjusted. Suitable normalized count rate values for one embodiment of the present invention are shown in Table 1. It will be recognized that other suitable normalized count rate values may be derived or selected in accordance with the present invention.

In calculation block 102 SUM1 is multiplied by sixteen to normalize SUM1 for comparison with SUM16. It will be recognized that, alternatively, SUM16 could be normalized for comparison with SUM1 by dividing SUM16 by 16. The normalized value of SUM1 is used to select the bin from bin array 91 which includes the normalized value of SUM1. The value of SUM16 is used to select the bin in bin array 91 which includes the normalized value of SUM16. If the bin which includes the normalized value of SUM1 is separated from the bin which includes the normalized value of SUM16 by at least one whole bin of bin array 91, then the normalized value of SUM1 may be used as the current count rate. Since it is known from the a-priori selection of bin array 91 values that the current count rate is statistically significantly different if it resides at least one bin width away from the value of SUM16, the SUM1 is a better estimate of count rate, and should be used as the new current count rate. If the normalized value of SUM1 is selected as the current count rate, the count rate determination algorithm then terminates and an audible output pitch is determined as described in association with FIGS. 14, 15, and 16.

TABLE 1.

Bin Array 91 values

| BIN | TOP OF BIN COUNT RATE (CPS) | TOP OF BIN NUMBER OF COUNTS |
|---|---|---|
| 1 | 16 | 16 |
| 2 | 98 | 100 |
| 3 | 238 | 243 |
| 4 | 437 | 447 |
| 5 | 694 | 711 |
| 6 | 1010 | 1034 |
| 7 | 1384 | 1418 |
| 8 | 1818 | 1861 |
| 9 | 2309 | 2365 |
| 10 | 2860 | 2928 |
| 11 | 3468 | 3552 |
| 12 | 4136 | 4235 |
| 13 | 4862 | 4979 |
| 14 | 5647 | 5782 |
| 15 | 6490 | 6646 |

If the product of SUM1 multiplied by sixteen is within one bin width of bin array 91 of SUM16, then it is known that the current count in element one of array 60 is not significant and should not be used as the new current count rate. In this case the non-linear count rate evaluation algorithm continues on to the next step A 105 illustrated in FIG. 11.

Figure 11:
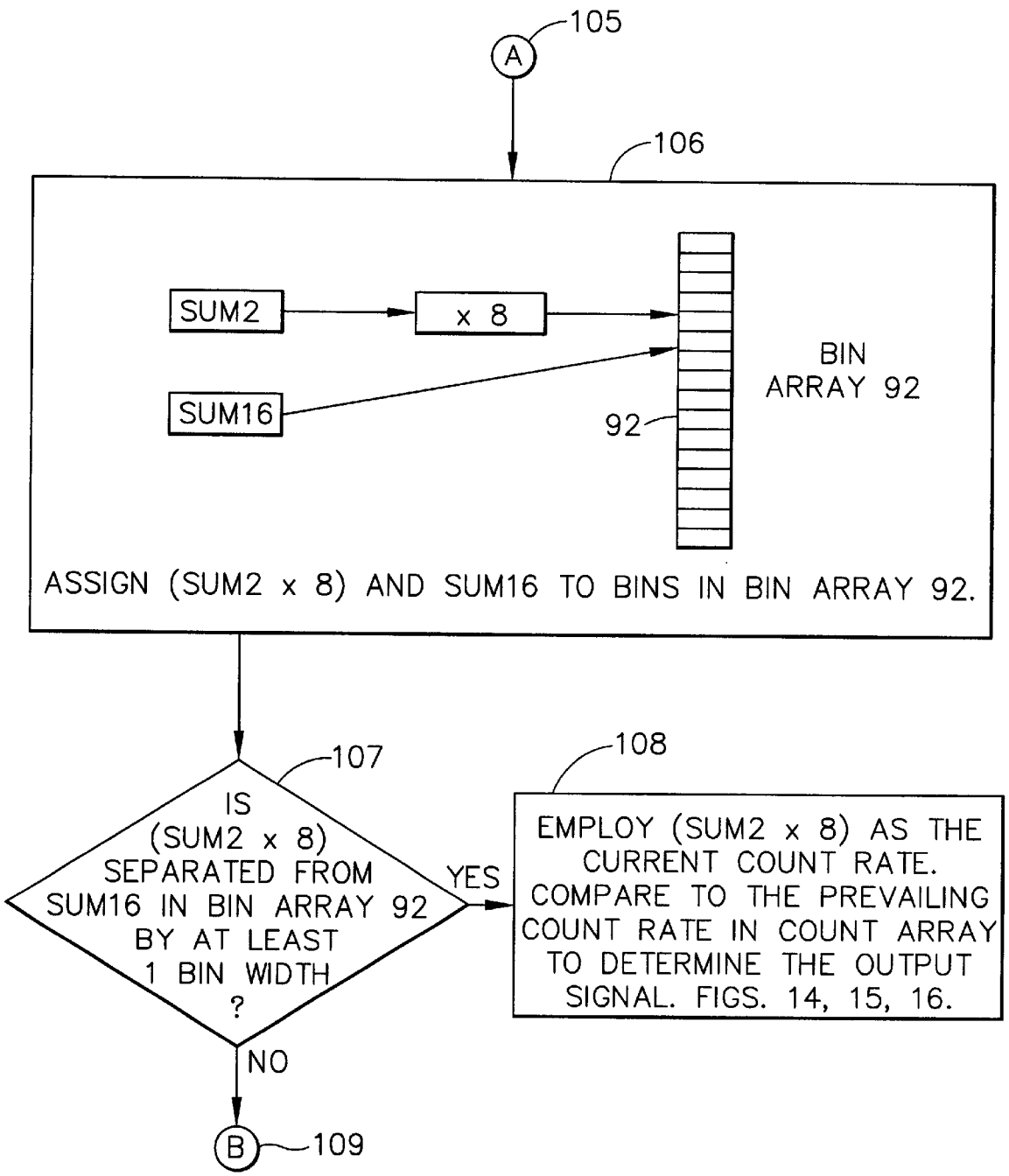
FIG. 11 is the continuation of a flowchart illustrating a method of data analysis in accordance with the present invention relating to SUM2.

In FIG. 11, calculation block 106 illustrates a method of normalizing SUM2 and comparing SUM2 to SUM16 in accordance with the present invention. FIG. 11 illustrates point A 105, calculation block 106, decision 107, decision yes result 108, and point B 109. The step of the count rate determination algorithm illustrated in calculation block 106 determines if a normalized SUM2 is statistically distinct from SUM16. One method of accomplishing this is by developing a bin array 92 which includes a series of bins, each bin containing a range of normalized count rates, wherein the normalized count rates in each bin are selected to be statistically different from the normalized count rates in bins one bin away from the selected bin. Normalized count rate values for each bin in bin array 92 are predetermined and, in the present embodiment may be calculated using statistical t-tests and empirically adjusted. Suitable normalize count rate values for one embodiment of the present invention are shown in Table 2. It will be recognized that other suitable normalized count rate values may be derived or selected in accordance with the present invention.

In calculation block 106, SUM2 is multiplied by eight to normalize SUM2 for comparison with SUM16. It will be recognized that, alternatively, SUM16 could be normalized for comparison with SUM2 by dividing SUM16 by 8. The normalized value of SUM2 is used to select the bin from bin array 92 which includes the normalized value of SUM2. The value of SUM16 is used to select the bin in bin array 92 which includes the normalized value of SUM16. If the bin which includes the normalized value of SUM2 is separated from the bin which includes the normalized value of SUM16 by at least one whole bin of bin array 92, then the normalized value of SUM2 may be used as the current count rate. Since it is known from the a-priori selection of bin array 92 values that the current count rate is statistically significantly different if it resides at least one bin width away from the value of SUM16, then SUM2 is a better estimate of count rate, and should be used as the new current count rate. If the normalized value of SUM2 is selected as the current count rate, the count rate determination algorithm then terminates and an audible output pitch is determined as described in association with FIGS. 14, 15, and 16.

TABLE 2.

Bin Array 92 values

| BIN | TOP OF BIN COUNT RATE (CPS) | TOP OF BIN NUMBER OF COUNTS |
|---|---|---|
| 1 | 8 | 8 |
| 2 | 47 | 48 |
| 3 | 113 | 115 |
| 4 | 206 | 211 |
| 5 | 327 | 335 |
| 6 | 475 | 486 |
| 7 | 650 | 666 |
| 8 | 853 | 873 |
| 9 | 1083 | 1109 |
| 10 | 1340 | 1372 |
| 11 | 1625 | 1664 |
| 12 | 1937 | 1984 |
| 13 | 2277 | 2331 |
| 14 | 2643 | 2707 |
| 15 | 3038 | 3110 |
| 16 | 3459 | 3542 |
| 17 | 3908 | 4002 |
| 18 | 4384 | 4489 |
| 19 | 4887 | 5005 |
| 20 | 5418 | 5548 |
| 21 | 5977 | 6120 |

Figure 12:
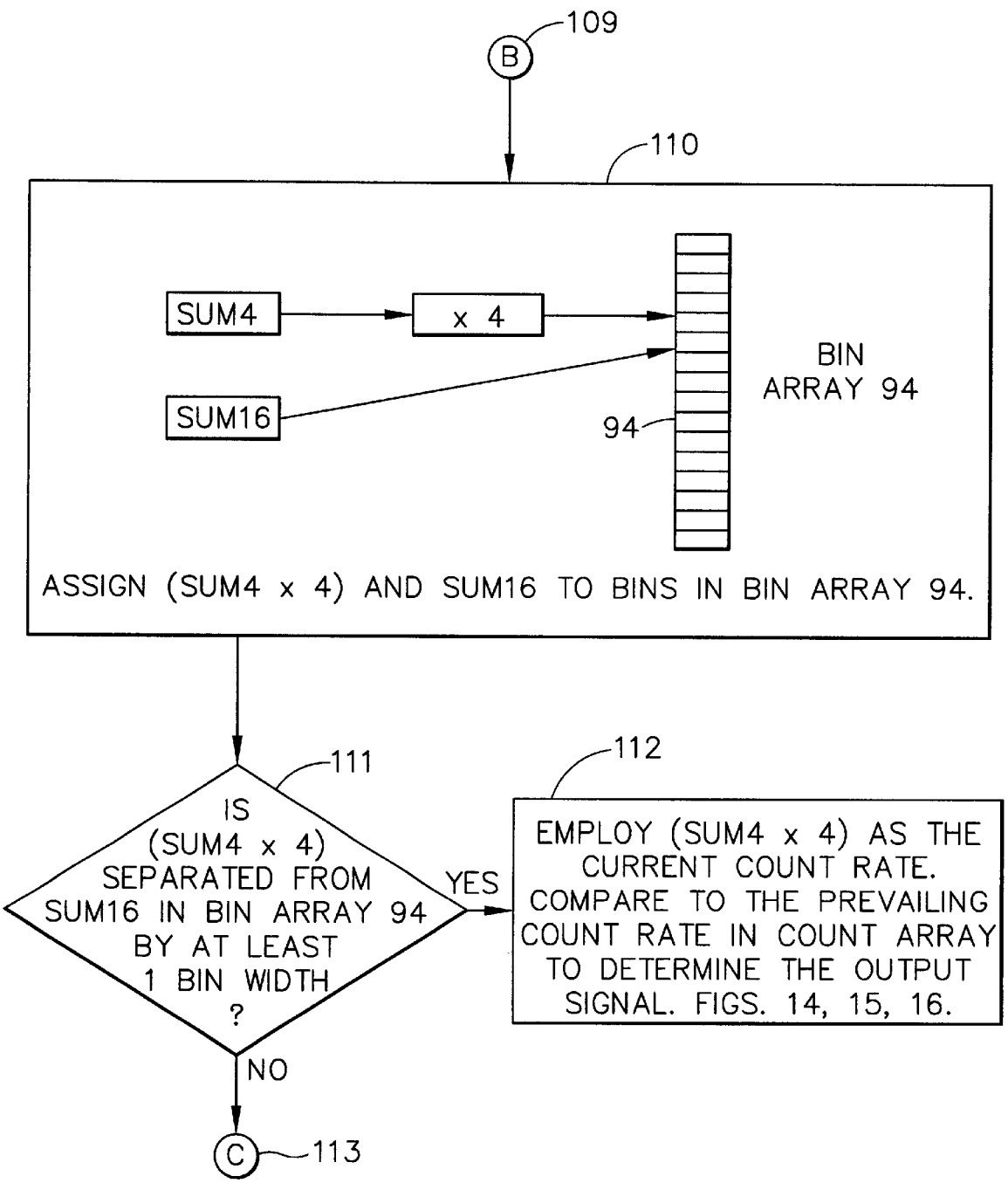
FIG. 12 is the continuation of a flowchart illustrating a method of data analysis in accordance with the present invention relating to SUM4.

In FIG. 12, calculation block 110 illustrates a method of normalizing SUM4 and comparing SUM4 to SUM16 in accordance with the present invention. FIG. 12 illustrates point B 109, calculation block 110, decision 111, decision yes result 112, and point C 113. The step of the count rate determination algorithm illustrated in calculation block 110 determines if a normalized SUM4 is statistically distinct from SUM16. One method of accomplishing this is by developing a bin array 94 which includes a series of bins, each bin containing a range of normalized count rates, wherein the normalized count rates in each bin are selected to be statistically different from the normalized count rates in bins one bin away from the selected bin. Normalized count rate values for each bin in bin array 94 are predetermined and, in the present embodiment may be calculated using statistical t-tests and empirically adjusted. Suitable normalized count rate values for one embodiment of the present invention are shown in Table 3. It will be recognized that other suitable normalized count rate values may be derived or selected in accordance with the present invention.

In calculation block 110, SUM4 is multiplied by four to normalize SUM4 for comparison with SUM16. It will be recognized that, alternatively, SUM16 could be normalized for comparison with SUM4 by dividing SUM16 by 4. The normalized value of SUM4 is used to select the bin from bin array 94 which includes the normalized value of SUM4. The value of SUM16 is used to select the bin in bin array 94 which includes the normalized value of SUM16. If the bin which includes the normalized value of SUM4 is separated from the bin which includes the normalized value of SUM16 by at least one whole bin of bin array 94, then the normalized value of SUM4 may be used as the current count rate. Since it is known from the a-priori selection of bin array 94 values that the current count rate is statistically significantly different if it resides at least one bin width away from the value of SUM16, then SUM4 is a better estimate of count rate, and should be used as the new current count rate. If the normalized value of SUM4 is selected as the current count rate, the count rate determination algorithm then terminates and an audible output pitch is determined as described in association with FIGS. 14, 15, and 16.

TABLE 3.

Bin Array 94 values

| BIN | TOP OF BIN COUNT RATE (CPS) | TOP OF BIN NUMBER OF COUNTS |
|---|---|---|
| 1 | 4 | 4 |
| 2 | 21 | 22 |
| 3 | 50 | 51 |
| 4 | 91 | 93 |
| 5 | 143 | 146 |
| 6 | 207 | 212 |
| 7 | 283 | 290 |
| 8 | 370 | 379 |
| 9 | 470 | 481 |
| 10 | 580 | 594 |
| 11 | 703 | 720 |
| 12 | 837 | 858 |
| 13 | 984 | 1007 |
| 14 | 1141 | 1169 |
| 15 | 1311 | 1342 |
| 16 | 1492 | 1528 |
| 17 | 1685 | 1726 |
| 18 | 1890 | 1935 |
| 19 | 2106 | 2157 |
| 20 | 2334 | 2390 |
| 21 | 2574 | 2636 |
| 22 | 2826 | 2893 |
| 23 | 3089 | 3163 |
| 24 | 3364 | 3445 |
| 25 | 3651 | 3738 |
| 26 | 3949 | 4044 |
| 27 | 4259 | 4361 |

TABLE 3.-continued

Bin Array 94 values

| BIN | TOP OF BIN COUNT RATE (CPS) | TOP OF BIN NUMBER OF COUNTS |
|---|---|---|
| 28 | 4581 | 4691 |
| 29 | 4915 | 5033 |
| 30 | 5260 | 5386 |
| 31 | 5617 | 5752 |
| 32 | 5986 | 6129 |

Figure 13:
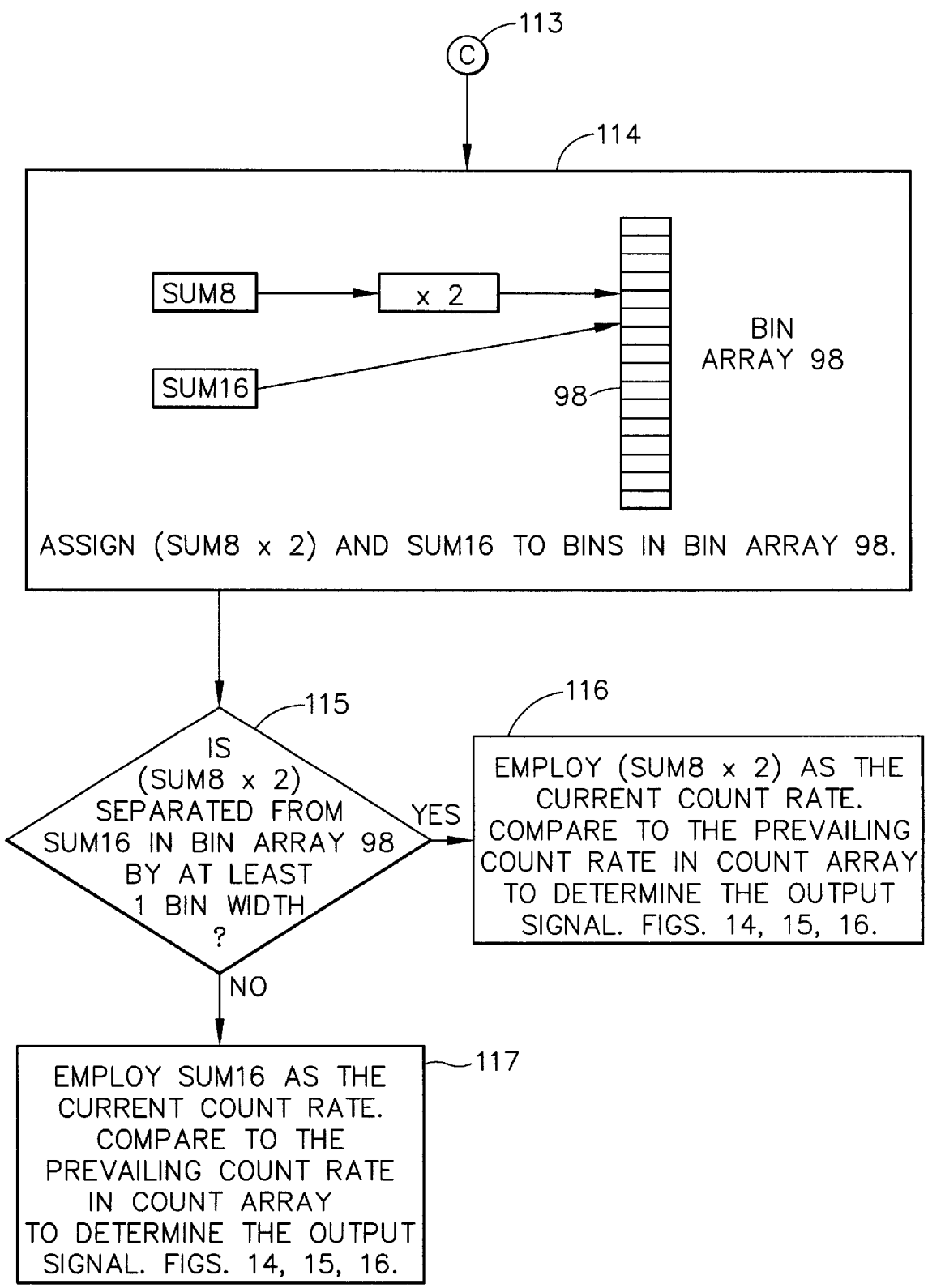
FIG. 13 is the continuation of a flowchart illustrating a method of data analysis in accordance with the present invention relating to SUM8.

In FIG. 13, calculation block 114 illustrates a method of normalizing SUM8 and comparing SUM8 to SUM16 in accordance with the present invention. FIG. 13 illustrates point C 113, calculation block 114, decision 115, decision yes result 116, and decision no result 117. The step of the count rate determination algorithm illustrated in calculation block 114 determines if a normalized SUM8 is statistically distinct from SUM16. One method of accomplishing this is by developing a bin array 98 which includes a series of bins, each bin containing a range of normalized count rates, wherein the normalized count rates in each bin are selected to be statistically different from the normalized count rates in bins one bin away from the selected bin. Normalized count rate values for each bin in bin array 98 are predetermined and, in the present embodiment may be calculated using statistical t-tests and empirically adjusted. Suitable normalized count rate values for one embodiment of the present invention are shown in Table 4. It will be recognized that other suitable normalized count rate values may be derived or selected in accordance with the present invention.

In calculation block 114, SUM8 is multiplied by two to normalize SUM8 for comparison with SUM16. It will be recognized that, alternatively, SUM16 could be normalized for comparison with SUM8 by dividing SUM16 by 2. The normalized value of SUM8 is used to select the bin from bin array 98 which includes the normalized value of SUM8. The value of SUM16 is used to select the bin in bin array 98 which includes the normalized value of SUM16. If the bin which includes the normalized value of SUM8 is separated from the bin which includes the normalized value of SUM16 by at least one whole bin of bin array 98, then the normalized value of SUM8 may be used as the current count rate. Since it is known from the a-priori selection of bin array 98 values that the current count rate is statistically significantly different if it resides at least one bin width away from the value of SUM16, then SUM8 is a better estimate of count rate, and should be used as the new current count rate. If the normalized value of SUM8 is selected as the current count rate, the count rate determination algorithm then terminates and an audible output pitch is determined as described in association with FIGS. 14, 15, and 16.

TABLE 4.

Bin Array 98 values

| BIN | TOP OF BIN COUNT RATE (CPS) | TOP OF BIN NUMBER OF COUNTS |
|---|---|---|
| 1 | 2 | 2 |
| 2 | 8 | 9 |
| 3 | 19 | 19 |
| 4 | 33 | 34 |
| 5 | 51 | 52 |
| 6 | 73 | 75 |
| 7 | 99 | 101 |

TABLE 4.-continued

Bin Array 98 values

| BIN | TOP OF BIN COUNT RATE (CPS) | TOP OF BIN NUMBER OF COUNTS |
|---|---|---|
| 8 | 129 | 132 |
| 9 | 162 | 166 |
| 10 | 200 | 205 |
| 11 | 241 | 247 |
| 12 | 287 | 294 |
| 13 | 336 | 344 |
| 14 | 389 | 399 |
| 15 | 447 | 457 |
| 16 | 508 | 520 |
| 17 | 573 | 586 |
| 18 | 641 | 657 |
| 19 | 714 | 731 |
| 20 | 791 | 810 |
| 21 | 871 | 892 |
| 22 | 956 | 979 |
| 23 | 1044 | 1069 |
| 24 | 1137 | 1164 |
| 25 | 1233 | 1262 |
| 26 | 1333 | 1365 |
| 27 | 1437 | 1471 |
| 28 | 1545 | 1582 |
| 29 | 1657 | 1696 |
| 30 | 1772 | 1815 |
| 31 | 1892 | 1937 |
| 32 | 2016 | 2064 |
| 33 | 2143 | 2195 |
| 34 | 2274 | 2329 |
| 35 | 2410 | 2468 |
| 36 | 2549 | 2610 |
| 37 | 2692 | 2757 |
| 38 | 2839 | 2907 |
| 39 | 2990 | 3062 |
| 40 | 3145 | 3220 |
| 41 | 3303 | 3383 |
| 42 | 3466 | 3549 |
| 43 | 3632 | 3720 |
| 44 | 3803 | 3894 |
| 45 | 3977 | 4073 |
| 46 | 4155 | 4255 |
| 47 | 4338 | 4442 |
| 48 | 4524 | 4632 |
| 49 | 4714 | 4827 |
| 50 | 4907 | 5025 |
| 51 | 5105 | 5228 |
| 52 | 5307 | 5434 |
| 53 | 5513 | 5645 |

If the normalized value of SUM1, SUM2, SUM4 or SUM8 are not selected as the new current count rate, then the new current count rate is SUM16. If SUM16 is selected as the current count rate, the count rate determination algorithm then terminates and an audible output pitch is determined as described in association with FIGS. 14, 15, and 16.

Given the information presented in discussing FIGS. 10–13, it is now possible to define a heuristic non-linear count rate evaluation algorithm. A heuristic non-linear count rate evaluation algorithm performs an operation in which the output count rate calculated does not satisfy the rule of superposition, and wherein a decision or selection from multiple possible count rates is made based on selection criteria. For example, the algorithm described along with FIGS. 10–13 would be in a family of heuristic non-linear count rate evaluation algorithms, with the selection criterion being the statistically significant count rate change having the quickest system response time.

Figure 14:
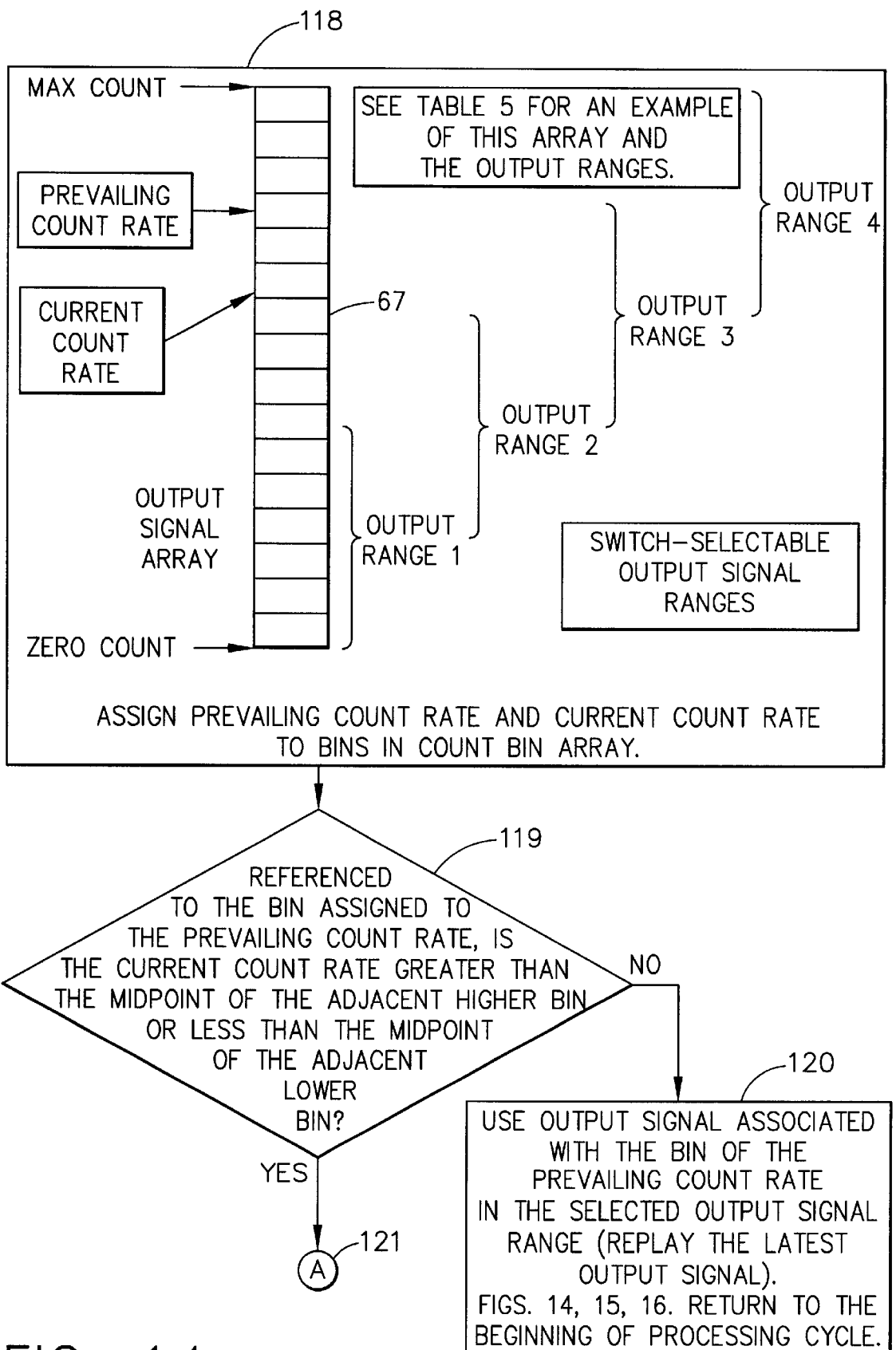
FIG. 14 is a portion of a flowchart illustrating a method of providing an audible pitch signal to the operator.
Figure 15:
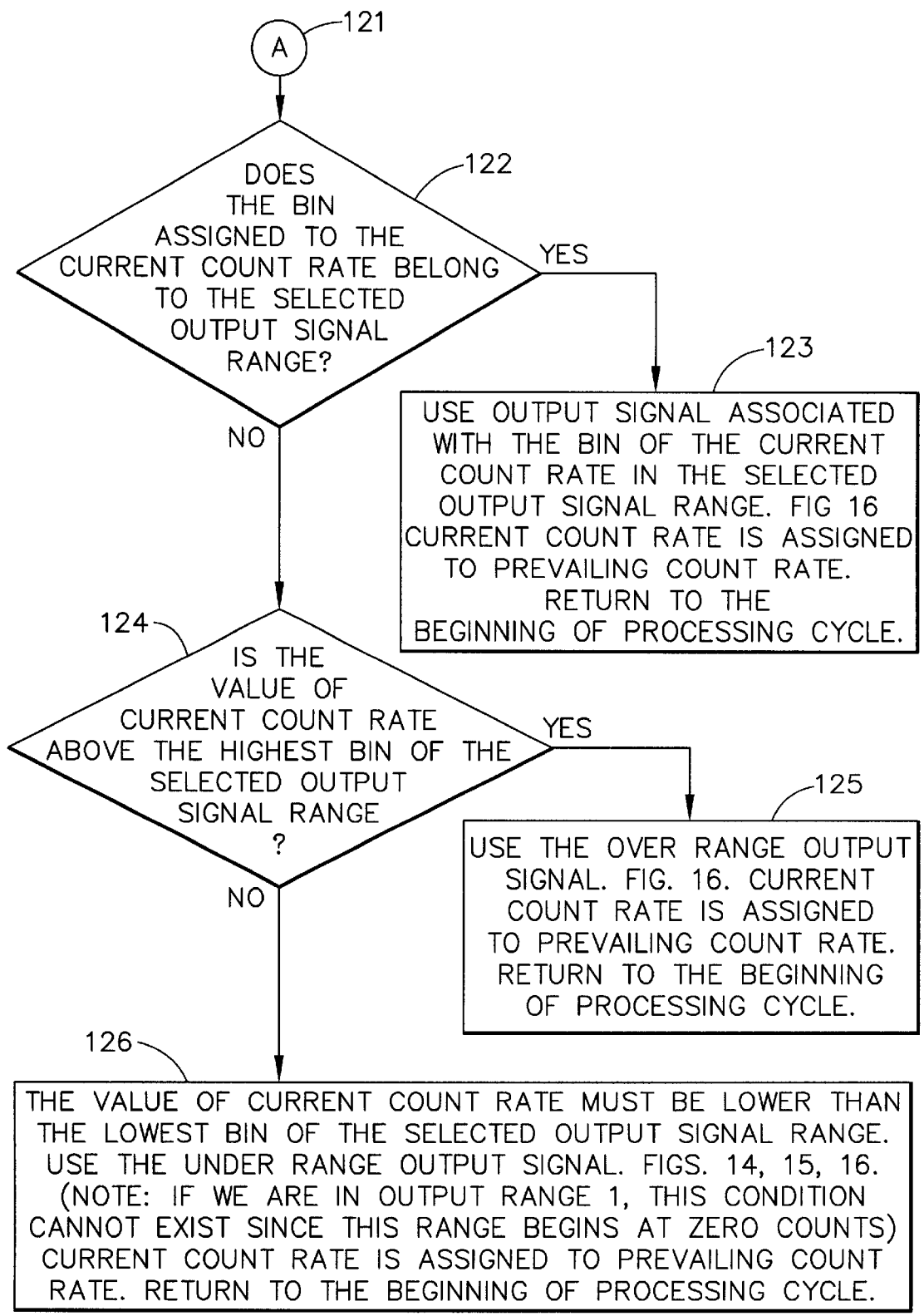
FIG. 15 is a continuation of the flowchart illustrating a method of providing an audible pitch signal to the operator.
Figure 16:
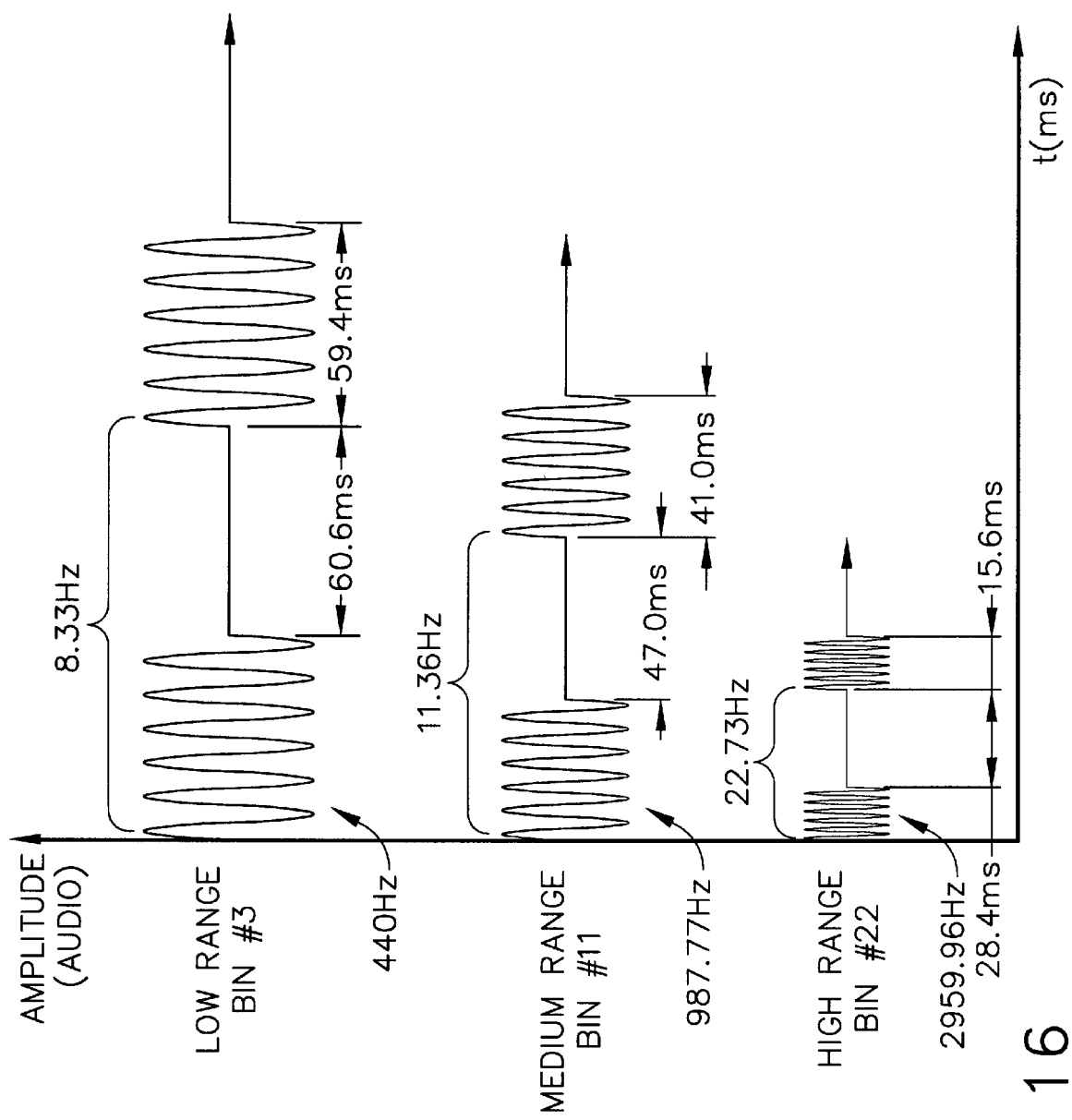
FIG. 16 illustrates the selection of an audible signal corresponding to changes in count rate information.

FIGS. 14, 15, and 16 illustrate a method of providing an audible pitch signal to the operator. It is important to present audio cues to the operator that are intuitive for the operation of an audible guidance system. Table 5 presents a range of count rates that an operator needs to discern during audible guidance for sentinel node procedures. It is difficult for an operator to discern 70 unique discrete levels. It was discovered that using a single known scale, such as, for example, the A-major musical scale, is the best intuitive feedback for increasing or decreasing count rates.

Change in frequency should be based on a musical scale optimizing the human audible range. Each output range comprises a series of array bins wherein each array bin corresponds to a distinct sound file. From the lowest to the highest bin, the pitch increases in increments corresponding to the A-major scale in music. The sounds are repetitive, with frequency increasing and duration decreasing monotonically from lowest to highest output signal. An exception exists for output signal range 1; the lowest bin results in no output signal. If the current count rate corresponds to a output signal that is over or under the current output range selected, then an over range, or an under range, signal is used respectively. In event of a lost signal, or zero count rate, then no output audible signal is produced.

Modulating another parameter of the sound in order to cue the operator to the relative pitch facilitates pitch discrimination. As the input count rate increases, sound pulse increases in repetition rate, with the pitch of each pulse rising correspondingly. It was discovered that reinforcing the scale with a repetition rate 66, and a duty cycle, compounds the intuitive nature of discernable change over a wider range of operator perception variability. Audible output signals should have a minimum of 150 millisecond total pulse duration, including rise and fall.

Louder sounds appear higher in frequency than the same sound played at a lower volume. Wherever frequency modulation is used the amplitude of the pitch must be adjusted such that the perceived volume is constant. Volumes may be adjusted such that the apparent audible loudness perceived by the operator is constant. This may be accomplished by adjusting the actual audible output pulse amplitude according to a predefined correction such as the dB-A human perception audible spectral response.

The human audible range of frequencies is generally accepted to be from 20 Hertz to 20,000 Hertz, however the most sensitive range for the majority of operators is between 1000 and 3000 Hertz. Due to the limited hearing range of human perception, and possible hearing losses of operators, a range of approximately 300 hertz to 4000 hertz was selected as optimal. Dividing this range into an A-major scale results in about 24 distinct frequencies, and necessitates the separation of the total range of possible count rates, shown in Table 5, into four ranges, shown in FIG. 14 as output range 1, output range 2, output range 3, and output range 4. Output ranges may be overlapped, as shown in Table 5, to allow for count rate variation before and after a range shift is completed.

A triangular waveform utilizing multiple frequencies and timbre adds to the esthetic value of sound and contributes to perceived "pleasantness". Also the addition of a number of harmonics to the fundamental could be used to represent a change in count rate. For example, the greater the number of harmonics, the greater the difference from the baseline or background counts is perceived to be. Adding a single harmonic of a given multiple might also be used to signal a change, with a higher frequency multiple indicating greater change.

TABLE 5

Count Rate Ranges

| | | |
|---|---|---|
| COUNT BIN ARRAY | | |
| z (confidence factor) | 1.28 | |
| max integration time | 1.024 | sec |
| time per FIFO bin | 0.054 | sec |
| *bins in FIFO array | 16 | |

| BIN | TOP OF BIN COUNT RATE (CPS) | TOP OF BIN NUMBER OF COUNTS |
|---|---|---|
| 1 | 1 | 1 |
| 2 | 4 | 4 |
| 3 | 8 | 8 |
| 4 | 14 | 14 |
| 5 | 22 | 22 |
| 6 | 31 | 31 |
| 7 | 41 | 42 |
| 8 | 54 | 55 |
| 9 | 68 | 69 |
| 10 | 83 | 85 |
| 11 | 100 | 103 |
| 12 | 119 | 122 |
| 13 | 139 | 143 |
| 14 | 161 | 165 |
| 15 | 185 | 189 |
| 16 | 210 | 215 |
| 17 | 237 | 243 |
| 18 | 265 | 272 |
| 19 | 295 | 302 |
| 20 | 327 | 334 |
| 21 | 360 | 368 |
| 22 | 395 | 404 |
| 23 | 431 | 441 |
| 24 | 469 | 480 |
| 25 | 508 | 521 |
| 26 | 549 | 563 |
| 27 | 592 | 606 |
| 28 | 637 | 652 |
| 29 | 683 | 699 |
| 30 | 730 | 748 |
| 31 | 779 | 798 |
| 32 | 830 | 850 |
| 33 | 882 | 903 |
| 34 | 935 | 959 |
| 35 | 992 | 1016 |
| 36 | 1049 | 1074 |
| 37 | 1108 | 1134 |
| 38 | 1168 | 1196 |
| 39 | 1230 | 1259 |
| 40 | 1293 | 1324 |
| 41 | 1359 | 1391 |
| 42 | 1425 | 1460 |
| 43 | 1494 | 1530 |
| 44 | 1564 | 1601 |
| 45 | 1635 | 1674 |
| 46 | 1708 | 1749 |
| 47 | 1783 | 1826 |
| 48 | 1859 | 1904 |
| 49 | 1937 | 1984 |
| 50 | 2017 | 2065 |
| 51 | 2098 | 2148 |
| 52 | 2181 | 2233 |
| 53 | 2265 | 2319 |
| 54 | 2351 | 2407 |
| 55 | 2439 | 2497 |
| 56 | 2528 | 2588 |
| 57 | 2618 | 2681 |
| 58 | 2711 | 2776 |
| 59 | 2805 | 2872 |
| 60 | 2900 | 2970 |
| 61 | 2997 | 3069 |
| 62 | 3096 | 3170 |
| 63 | 3196 | 3273 |
| 64 | 3298 | 3378 |
| 65 | 3402 | 3484 |
| 66 | 3507 | 3591 |
| 67 | 3614 | 3701 |
| 68 | 3722 | 3812 |
| 69 | 3832 | 3924 |
| 70 | 3944 | 4038 |

Range 1: bins 1–16
Range 2: bins 17–31
Range 3: bins 32–47
Range 4: bins 48–70

It is necessary to cue the operator when a shift is required between ranges, and in which direction the range should be shifted. The operator's attention is focused on identifying sentinel node location, and must be re-directed to address an output range shift. It was discovered that providing a continuous pitch to the operator, in lieu of the repetition rate 66, intuitively cures the operator to shift ranges. It was also discovered that three successive beeps of pitch intuitively indicate a completion of a task to the operator.

FIG. 14 illustrates comparing the prevailing count rate to the current count rate from one of the steps illustrated in FIGS. 10–13. FIG. 14 illustrates array 67 calculation block 118, separation decision 119, no separation 120, and point A 121. Suitable values for array 67 of an embodiment of the current invention are shown in Table 5.

In FIG. 14, calculation block 118 illustrates a method of comparing the prevailing count rate to a current count rate. Output signal array 67 illustrated in calculation block 118 determines if a prevailing count rate is statistically distinct from a current count rate. One method of accomplishing this is by developing an output signal array 67 which includes a series of bins, each bin containing a range of count rates, wherein the count rates in each bin are selected to be statistically different from the count rates in bins one bin away from the selected bin. Count rate values for each bin in output signal array 67 are predetermined and, in the present embodiment, were calculated using human response information gathered empirically. In one embodiment of the present invention, the a value is said to be statistically different for the purposes of this calculation if it is past the midpoint of the values in a neighboring bin. Therefore, for example, if the current count rate is in the same bin as the prevailing count rate or if the current count rate is in an adjacent bin, but not past the midpoint value of the adjacent bin, the prevailing count rate is used to select the appropriate audio output signal. If, on the other hand, the current count rate is not in the same bin as the prevailing count rate and is past the midpoint of the adjacent bin, then the current count rate will be used to select the appropriate audio output signal and will become the new prevailing count rate. Suitable count rate values for one embodiment of the present invention are shown in Table 5. It will be recognized that other suitable count rate values may be derived or selected in accordance with the present invention.

Separation decision 119 checks whether the prevailing count rate and the current count rate are sufficiently different to merit a change in the signal output of audio speaker 58 illustrated in FIG. 1. Note that for any count bin array location within an output range, a prevailing count rate will have a distinct pitch and repetition rate as described in Tables 5 and 6. However, multiple options for pitch and repetition rate are available for a single prevailing count rate depending on which current output range is selected by the operator.

TABLE 6.

Output Range 1

| Bin Number | Pitch [Hz] | Repetition Frequency [Hz] | Period (ms) | On (ms) | Off (ms) |
|---|---|---|---|---|---|
| Under | 329.63 | Continuous Tone | | | |
| 1 | 369.99 | 7.81 | 128 | 64 | 64 |
| 2 | 415.30 | 8.06 | 124 | 61.7 | 62.3 |
| 3 | 440.00 | 8.33 | 120 | 59.4 | 60.6 |
| 4 | 493.88 | 8.62 | 116 | 57.1 | 58.9 |
| 5 | 554.37 | 8.93 | 112 | 54.8 | 57.2 |
| 6 | 587.33 | 9.26 | 108 | 52.5 | 55.5 |
| 7 | 659.26 | 9.62 | 104 | 50.2 | 53.8 |
| 8 | 739.99 | 10.00 | 100 | 47.9 | 52.1 |
| 9 | 830.61 | 10.42 | 96 | 45.6 | 50.4 |
| 10 | 880.00 | 10.87 | 92 | 43.3 | 48.7 |
| 11 | 987.77 | 11.36 | 88 | 41.0 | 47.0 |
| 12 | 1108.73 | 11.90 | 84 | 38.7 | 45.3 |
| 13 | 1174.66 | 12.50 | 80 | 36.3 | 43.7 |
| 14 | 1318.51 | 13.16 | 76 | 34.0 | 42.0 |
| 15 | 1479.98 | 13.89 | 72 | 31.7 | 40.3 |

TABLE 6.-continued

Output Range 1

| Bin Number | Pitch [Hz] | Repetition Frequency [Hz] | Period (ms) | On (ms) | Off (ms) |
|---|---|---|---|---|---|
| 16 | 1661.22 | 14.71 | 68 | 29.4 | 38.6 |
| 17 | 1760.00 | 15.63 | 64 | 27.1 | 36.9 |
| 18 | 1975.53 | 16.67 | 60 | 24.8 | 35.2 |
| 19 | 2217.46 | 17.86 | 56 | 22.5 | 33.5 |
| 20 | 2349.32 | 19.23 | 52 | 20.2 | 31.8 |
| 21 | 2637.02 | 20.83 | 48 | 17.9 | 30.1 |
| 22 | 2959.96 | 22.73 | 44 | 15.6 | 28.4 |
| 23 | 3322.44 | 25.00 | 40 | 13.3 | 26.7 |
| 24 | 3520.00 | 27.78 | 36 | 11 | 25 |
| Over | 3951.07 | Continuous Tone | | | |

FIG. 15 is a continuation of the flow chart illustrated in FIG. 14. FIG. 15 illustrates point A 121, current range decision 122, range yes result 123, out of range decision 124, out of range yes result 125, and under range result 126. Depending on which output signal array 67 range is selected, a range output signal for audio speaker 58 is determined according to out of range decision 124, and current range decision 122. If the current count rate is within range, a range yes result 123 occurs, and the prevailing count rate is updated. If the current count rate is over or under range, out of range yes result 125 and under range result 126 are acted on respectively.

FIG. 16 illustrates the selection of an audible signal corresponding to changes in count rate information. The prevailing count rate establishes a bin location in an output signal array 67 illustrated in FIG. 14. Each output signal array 67 range corresponds to a series of distinct sound files. From the lowest to the highest output signal, the pitch increases in increments corresponding to the A-major scale in music. The sounds are repetitive with frequency increasing and duration decreasing monotonically from lowest to highest array bin. (See FIG. 16 and Table 6) Two exceptions to the pitch generation process occur. For output signal range 1, the lowest signal results in no output signal (no audible pitch). For output signal ranges 2, 3, and 4, if the prevailing count rate becomes zero, no audible pitch is generated.

Depending on which output range is selected, a selected output signal range of output signal array 67 will be selected. If the current count rate corresponds to a output signal array 67 bin that is over or under the selected output range, then an over range or an under range signal is used respectively. (See Table 6) As the prevailing count rate increases within an output range, both pulse frequency and repetition rate increase as defined by the equal temperament scale. Pulse duration also decreases as illustrated in FIG. 16.

Returning now to FIG. 1 with an understanding of a non-linear audible guidance system 10, the improved response of an audible guidance system 10 may be used advantageously in a procedure to detect and remove sentinel nodes 81. Two types of probes are available for use with audible guidance system 10. A scanning gamma probe 20 is used for mapping or surveying lymph nodes extracorporeally to locate areas of localized radiation emission which may be associated with sentinel nodes. A targeting probe 25 is used to detect and isolate nodes intracorporeally during the surgical removal of sentinal nodes.

Referring to FIGS. 6 and 7, a hand-held radiation detecting gamma probe 20 is provided which supports a scintillator 46 of sufficient surface area to detect the minute levels of radiation involved in the procedure. The gamma probe 20 currently utilizes a Cesium Iodide scintillator 46 crystal of the noted adequate surface area, which is mounted in a "forward-looking" manner within a tubular probe body to facilitate its maneuvering in and about tissue. As the surgeon holds The gamma probe 20, the window 45 component thereof at its tip is moved along tissue being evaluated. During this surveying maneuver, as radiation is encountered, it is first evaluated for appropriate energy levels by discriminator 50, and then statistically evaluated in terms of count rates. Where a statistically significant change in count rate is encountered as determined by a non-linear algorithm, the prevailing count rate information is provided to the operator via a change in audible pitch.

Referring to FIGS. 1 and 8, as the operator moves the gamma probe 20 over the area of interest, scanning for radiolabled spots, the operator receives audible feedback in the form of pulses that change in pitch, repetition rate, duty cycle, and amplitude. When the gamma probe 20 is placed over a low count rate area or at a count rate at the low end of an output range, the operator hears a slow, low pitch pulsing. As the gamma probe 20 receives more radiation, both pitch and repetition rate increase. The use of frequencies corresponding to musical notes enables operators to clearly distinguish between areas that have similar but statistically different count rates. As the probe is moved back and forth between two such areas, the operator may rely more on changes in pitch rather than on an increase or decrease of repetition rate. In essence, changes in pitch allow for fine discrimination between similar input counts, while repetition rate is a quick and intuitive way of grossly distinguishing between high and low count areas.

Through the audible feedback (which is optimized for the human auditory range utilizing loudness, pitch, chroma, volume, pulse shape, duration, brightness, density, timbre, and temporal modulation) the operator will have a systematic more intuitive sense of use, therefore, ultimately benefiting the patient.

A sentinel node biopsy procedure in accordance with the present invention will generally follow the following step sequence. Steps may vary depending on surgeon preference. The description begins at the point of clinical diagnosis.

A biopsy is performed. Assuming the diagnosis is invasive ductal carcinoma, the patient and physician decide on breast procedure options. The patient is schedule for a breast procedure such as lumpectomy, segmentectomy or mastectomy.

On the day of the procedure, at least two hours (1–18+ hrs) before the procedure, the patient is injected with technetium 99 m sulfur colloid in saline solution>Dosage: typically 0.5–1.0 millicuries (0.5–3 millicuries), in a volume of 4 cc (1–6 cc). There are typically four to six 1 cc injections.

Palpable lesions: peritumoral injections

Nonpalpable lesions: Injections are placed adjacent to the biopsy cavity but not into the biopsy cavity Injections are not generally made into prior biopsy cavity.

Gently massage site after injection 5–10 min.

The patient waits in preoperative holding area until called for surgery. The patient is moved to the OR, and placed under general anesthesia. Ten minutes before incision, the surgeon injects 4–5 cc of blue dye (isosulfan blue or patent blue violet) in the same location where the technetium 99 sulfur colloid was injected (injection of a dye is not always performed). The injection site is gently massaged for approximately 5 minutes to aid the flow of the blue dye into the lymphatic vessels.

The scanning probe 36 is plugged into the control unit 15. The surgeon performs a preoperative transdermal scan of the axillary, supraclavicular and internal mammary region to identify the general location of the sentinel node(s). The radiolabeled node location is marked on the skin with the marker. The surgeon switches to the targeting probe 37. At the location of the skin mark, the surgeon makes an incision (3–6 cm). The surgeon scans inside the incision. Atraumatic dissection is performed in the direction of highest radiation counts. If blue dye is used, care is taken not to transect any blue lymphatic vessels encountered. The surgeon will follow the blue lymphatic vessel to locate the sentinel node(s).

Once a radiolabeled node is found an extended count rate analysis of the radioactivity is taken, in vivo, and recorded. The node may or may not be blue in color. The lymphatic vessels entering and leaving the node(s) are ligated, and then transected. The node is removed.

Once removed, the node is placed on top of the probe, with the probe pointing toward the ceiling. The actual count rate is recorded. The area is scanned again with the probe to verify no more radiolabeled nodes are present.

The surgeon closes the dissected tissue with standard surgical technique. The breast procedure (lumpectomy or mastectomy) is completed. The node(s) is sent to pathology for examination. Nodes may be held 36 hours to allow for radio-active decay before analysis.

The present method will now be laborated with respect to an example of particular anatomy and illustrations of FIGS. 8 and 9. Looking to FIGS. 8 and 9, an illustration of the scan region 32 is represented in general. At this scan region 32 there is depicted an internally disposed tumor 40. Looking to FIG. 9 the tumor 40 is shown in section, the pectoralis muscles being shown at 74 adjacent ribs 76 and intercostal muscle 80. The tumor 40 is located within breast 35 in conjunction with the lactiferous ductal system 86. By injecting a radiopharmaceutical in the vicinity of tumor 40, a procedure may be carried out to locate a sentinel node 81. A typical traverse for establishing the position of a sentinel node 44 is represented by dashed lines from gamma probe 20 initial posterior position 31 to anterior position 33. The sentinel node 81 will be, for example, present within the regional nodes of breast 35. As the sentinel node 81 is approached during the traversing of scan region 32, a substantial increase in count rate activity will be encountered, whereupon the node will be dissected and removed. The node will then be sent for pathologic examination.

The count rate may change substantially as a sentinel node is approached. As the prevailing count rate exceeds the range of audible output available for a giving setting, a continuous unique pitch will be presented to the system operator to indicate a suggested change of range. This functionality is also combined with the visual interface of display 17 range indicator 9 (FIG. 1) showing flashing arrows "up or down" to reinforce the audio feedback information. Actuating audio range swicth 23 will then set audible guidance system 10 to a new output range. The region of enhanced activity or sentinel node 81 is transversely traversed, for example, by moving gamma probe 20 along dashed lines from initial posterior position 31 to anterior position 33.

A small incision and tissue dissection then is performed and the procedure proceeds using, for example, targeting detector assembly 29 and audio range switch 23 thereof. Accordingly, the probe is moved deeper into torso 30 as sentinel node 81 is dissected out. Audio range switch 23 is actuated to maintain the audible output within discernable levels. The surgeon again may move the probe deeper, for example, and again carry out an audio range shift. A subsequent scan about sentinel node 81 may be performed to narrow and bracket the location of the sentinel node 81. At this juncture, only slight movement of the probe is required to complete a traverse and the location of the sentinel node is readily determined.

Sentinel node 81 then is excised and submitted for evaluation as to cancer involvement. When compared with the conventional surgical protocols of removing essentially all regional lymph nodes at the axilla, the minimally invasive aspect of the present methodology immediately becomes apparent.

If the operator is interested in knowing the count rates at multiple locations with a high degree of confidence, for example, to discriminate possible nodes, an extended count rate analysis may be performed as a separate mode of operation of audible guidance system 10. When the extended count rate analysis (ECRA) mode is activated an initialize single beep is heard and an hour glass icon appears on the display 17 (FIG. 1). After a count with desired statistical significance is accumulated a "success tone" of three beeps is heard and the final ECRA rate is displayed.

According to one embodiment of the present invention, the count rate determination algorithm is a non-linear algorithm. In order to define the scope of the current invention it is necessary to define the difference between a linear count rate determination algorithm and a non-linear count rate determination algorithm. A non-linear count rate determination algorithm performs an operation in which the output count rate calculated does not satisfy the rule of superposition. For example, if the output count rate calculated by an operation on the sum of two inputs is different than the sum of the output count rates calculated for each of the two inputs individually, then the operation is non-linear.

As an example of a linear count rate determination algorithm, if sixteen discrete count rates are provided as an input to a count rate determination algorithm over a given time interval, and the output count rate calculated is a weighted average of those sixteen discrete count rates, then the algorithm is a linear count rate determination algorithm. A squelching function subsequently applied to the output count rate may then result in a non-linear output of count rate information to the operator, but the squelching function is not determining the count rate itself. The squelching operation is merely used to determine if the current count rate will, or will not, be provided to the clinician.

It then follows that the algorithm disclosed in FIGS. 10–13 is a heuristic non-linear count rate determination algorithm.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method of radiation detection comprising the steps of:
   a) generating radiation decay rate counts wherein said counts comprise a sum of detection radiation decay evens over a time interval;
   b) loading said counts into an array;
   c) summing selected elements of said array to generate a total count and a plurality of candidate counts;
   d) comparing said total count to one of said candidate counts to determine whether said one of said candidate counts is statistically different from said total count;
   e) using said statistically different one of said candidate counts as an output count rate;
   f) generating an output signal using said output count rate to determine the characteristics of said output signal;
   g) partitioning said plurality of candidate counts into: a last count value at priority 1; a sum of the last two count values at priority 2; a sum of the last four count values at priority 3; a sum of the last eight count values at priority 4; said total count at priority 5; and
   h) selecting said one said candidate counts as the highest priority count value that is a statistically significant change from priority 5 said total count.

2. A method of radiation detection according to claim 1 wherein said candidate counts are normalized with respect to said total count.

3. A method of radiation detection according to claim 1 wherein said candidate counts are normalized with respect to said total count.

4. A method of radiation detection according to claim 1 wherein said last count value is directly proportional to the count in a first location of said array wherein said first location represents the most recent of said radiation decay rate counts.

5. A method of radiation detecting according to claim 1 wherein said output signal is an audible signal.

6. A method of radiation detection according to claim 5 wherein said audible signal is selected from a plurality of ranges wherein said plurality of ranges cover the entire range of possible count rates expected to be detected.

7. A method of radiation detection according to claim 6 wherein said output signal comprises an audible cue to shift from a first of said plurality of ranges to a second of said plurality of said ranges.

8. A method of locating radio-actively tagged sentinel lymph nodes comprising the steps of:
   a) injecting a patient with a radiopharmaceutical;
   b) providing a probe for converting radiation decay events into an electrical signal;
   c) discriminating said electrical signal from said probe into below threshold radiation decay events and above threshold radiation decay events;
   d) counting said above threshold radiation decay events over a plurality of at least 16 discrete time intervals;
   e) determining the best estimate of a current count rate by applying a non-linear filtering technique, comprising a heuristic non-linear count rate determination algorithm, to counts within said discrete time intervals; and
   f) providing a count rate output;
   g) providing an audible signal corresponding to the current count rate output of step f;
   h) providing a sound amplitude test and adjustment capability of the audible signal provided in step i.

9. A method of claim 8 wherein said non-linear filtering technique comprises heuristic non-linear count rate determination algorithm.

10. The method of claim 8 further comprising the steps of:
    i) partitioning said discrete time intervals into count rates corresponding to: a last count value at priority 1; a sum of the last two count values at priority 2; a sum of the last four count values at priority 3; a sum of the last eight count values at priority 4; a sum of the last sixteen count values at priority 5; and
    j) updating the count rate of step f as the highest priority count rate that is a statistically significant change from priority 5.

11. The method of claim 10 further comprising the step of:
    k) changing the audible signal from step i from a pulsed pitch to a continuous pitch after a predetermined count rate range has been exceeded.

* * * * *